US008239041B2

(12) United States Patent
Kondabatni et al.

(10) Patent No.: US 8,239,041 B2
(45) Date of Patent: Aug. 7, 2012

(54) MULTILAYER HELICAL WAVE FILTER FOR MEDICAL THERAPEUTIC OR DIAGNOSTIC APPLICATIONS

(75) Inventors: Kishore Kumar Kondabatni, Williamsville, NY (US); Warren S. Dabney, Orchard Park, NY (US); Robert Shawn Johnson, North Tonawanda, NY (US); Robert A. Stevenson, Canyon Country, CA (US); Christine A. Frysz, Orchard Park, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/193,501

(22) Filed: Jul. 28, 2011

(65) Prior Publication Data

US 2012/0029342 A1 Feb. 2, 2012

Related U.S. Application Data

(63) Continuation-in-part of application No. 12/873,862, filed on Sep. 1, 2010.

(60) Provisional application No. 61/369,822, filed on Aug. 2, 2010.

(51) Int. Cl.
*A61N 1/40* (2006.01)
(52) U.S. Cl. ...................................................... 607/116
(58) Field of Classification Search ........... 607/116–156
See application file for complete search history.

(56) References Cited

U.S. PATENT DOCUMENTS

| 3,980,975 | A | 9/1976 | Maxon, Jr. et al. |
| 4,236,127 | A | 11/1980 | Scherba |
| 5,217,010 | A | 6/1993 | Tsitlik et al. |
| 5,428,337 | A | 6/1995 | Vinclarelli et al. |
| 7,038,900 | B2 | 5/2006 | Stevenson et al. |
| 7,148,783 | B2 | 12/2006 | Parsche et al. |
| 7,363,090 | B2 | 4/2008 | Halperin et al. |
| 7,511,921 | B2 | 3/2009 | Mallary et al. |
| 7,561,906 | B2 | 7/2009 | Atalar et al. |
| 7,702,387 | B2 | 4/2010 | Stevenson et al. |
| 7,751,903 | B2 | 7/2010 | Stevenson et al. |
| 7,853,324 | B2 | 12/2010 | Stevenson et al. |
| 7,853,325 | B2 | 12/2010 | Dabney et al. |
| 7,899,551 | B2 | 3/2011 | Westlund et al. |
| 7,917,213 | B2 | 3/2011 | Bulkes et al. |
| 7,945,322 | B2 | 5/2011 | Stevenson et al. |
| 2003/0144720 | A1 | 7/2003 | Villaseca et al. |
| 2006/0041294 | A1 | 2/2006 | Gray |
| 2008/0049376 | A1 | 2/2008 | Stevenson et al. |
| 2008/0051854 | A1 | 2/2008 | Bulkes et al. |
| 2008/0243218 | A1 | 10/2008 | Bottomley et al. |
| 2008/0262584 | A1* | 10/2008 | Bottomley et al. ........... 607/119 |

(Continued)

*Primary Examiner* — Niketa Patel
*Assistant Examiner* — Hiba El-Kaissi
(74) *Attorney, Agent, or Firm* — Michael F. Scalise

(57) ABSTRACT

A multilayer helical wave filter having a primary resonance at a selected RF diagnostic or therapeutic frequency or frequency range, includes an elongated conductor forming at least a portion of an implantable medical lead. The elongated conductor includes a first helically wound segment having at least one planar surface, a first end and a second end, which forms a first inductive component, and a second helically wound segment having at least one planar surface, a first end and a second end, which forms a second inductive element. The first and second helically wound segments are wound in the same longitudinal direction and share a common longitudinal axis. Planar surfaces of the helically wound segments face one another, and a dielectric material is disposed between the facing planar surfaces of the helically wound segments and between adjacent coils of the helically wound segments, thereby forming a capacitance.

76 Claims, 22 Drawing Sheets

U.S. PATENT DOCUMENTS

| | | |
|---|---|---|
| 2009/0281592 A1 | 11/2009 | Vase |
| 2010/0010602 A1 | 1/2010 | Wedan et al. |
| 2010/0076538 A1 | 3/2010 | Desai et al. |
| 2010/0114277 A1 | 5/2010 | Zhao et al. |
| 2010/0160997 A1 | 6/2010 | Johnson et al. |
| 2010/0174348 A1 | 7/2010 | Bulkes et al. |
| 2010/0174349 A1 | 7/2010 | Stevenson et al. |
| 2010/0217262 A1 | 8/2010 | Stevenson et al. |
| 2010/0318164 A1 | 12/2010 | Chen et al. |
| 2011/0015713 A1 | 1/2011 | Min |
| 2011/0144734 A1 | 6/2011 | Westlund et al. |

* cited by examiner

UNIPOLAR

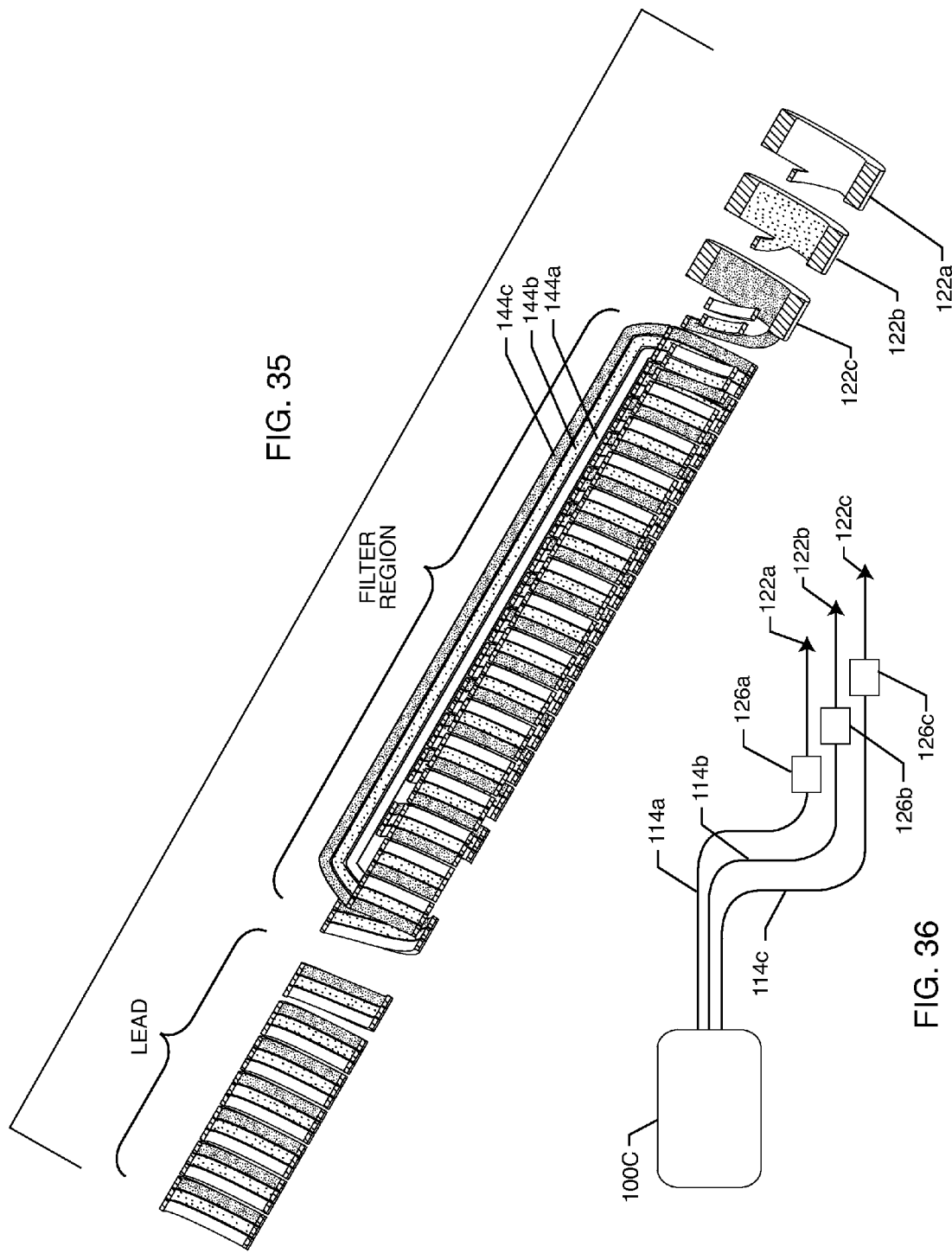

MULTILAYER HELICAL WAVE FILTER FOR MEDICAL THERAPEUTIC OR DIAGNOSTIC APPLICATIONS

FIELD OF THE INVENTION

This invention generally relates to the problem of high frequency energy induced onto implanted leads during medical diagnostic procedures such as magnetic resonant imaging (MRI). More specifically, the present invention relates to an implantable medical system comprised of an active medical device (AMD) and at least one lead extending exteriorly from a proximal end at or adjacent to the AMD, to a biological sensing or stimulating electrode at a distal end. The lead has at least one multilayer helical wave filter which is designed resonate at one or more MRI RF pulsed frequencies. At resonance, the multilayer helical wave filter presents a very high impedance in the lead system which impedes RF current flow thereby preventing overheating of the lead and/or its distal electrodes during exposure to high power radio frequency (RF) fields of a particular frequency and/or frequency range.

BACKGROUND OF THE INVENTION

The radio frequency (RF) pulsed field of an MRI scanner can couple to an implanted lead in such a way that electromagnetic forces (EMFs) are induced in the lead. The amount of energy that is induced is related to a number of complex factors, but in general is dependent upon the local electric field that is tangent to the lead and the integral of the electric field strength along the lead. In certain situations, these EMFs can cause RF currents to flow into distal electrodes or in the electrode interface with body tissue. It has been documented that when this current becomes excessive, overheating of said lead or its associated electrode(s) or overheating of the associated interface with body tissue can occur. There have been cases of damage to such body tissue which has resulted in loss of capture of cardiac pacemaking pulses or tissue damage severe enough to result in brain damage or multiple amputations, and the like.

Magnetic resonance imaging (MRI) is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AMDs after an MRI procedure, sometimes occurring many days later. Moreover, there are a number of papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There has been some progress in the design of active medical devices for specific use in an MRI environment under specified conditions. For example, Medtronic has received FDA approval for their REVO pacemaker, which is indicated at use for up to 2 watts per kilogram (Thorax scans excluded). St. Jude Medical and Biotronik have also received conditional approval for MRI pacemakers in Europe.

There are three types of electromagnetic fields used in an MRI unit. The first type is the main static magnetic field designated $B_0$ which is used to align protons in body tissue. The field strength varies from 0.5 to 3.0 Tesla in most of the commonly available MRI units in clinical use. Some of the newer research MRI system fields can go as high as 11.7 Tesla.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field which is circularly polarized in the actual plane; and (2) the H field, sometimes generally referred to as the net magnetic field in matter, which is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Lamour equation with the field strength of the main static field where: RF PULSED FREQUENCY in MHz=(42.56) (STATIC FIELD STRENGTH IN TESLA). There are also phosphorous and other types of scanners wherein the Lamour equation would be different. One also has to be concerned about harmonics that are produced by the MRI RF amplifier and birdcage coil of a typical MRI system. In addition to the main RF pulsed frequency, harmonics can also be deposited onto implanted leads.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements.

At the frequencies of interest in MRI, RF energy can be absorbed by body tissues (or elongated conductors) and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur.

The cause of heating in an MRI environment is twofold: (a) RF field coupling to the lead can occur which induces significant local heating; and (b) currents induced between the distal tip and tissue during MRI RF pulse transmission sequences can cause local Ohms Law heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing capture threshold (PCT), venous ablation, Larynx or esophageal ablation, myocardial perforation and lead penetration, or even arrhythmias caused by scar tissue. Such long term heating effects of MRI have not been well studied yet for all types of AMD lead geometries. There can also be localized heating problems associated with various types of electrodes in addition to tip electrodes. This includes ring electrodes or pad electrodes. Ring electrodes are commonly used with a wide variety of implanted device leads including cardiac pacemakers, and neurostimulators, and the like. Pad electrodes are very common in neurostimulator applications. For example, spinal cord stimulators or deep brain stimulators can include a plurality of pad electrodes (for example, 8.16 or 24 electrodes) to make contact with nerve tissue. A good example of this also occurs in a cochlear implant. In a typical cochlear implant there would be sixteen pad electrodes placed up into the cochlea. Several of these pad electrodes make contact with auditory nerves.

Variations in the pacemaker lead length and implant trajectory can significantly affect how much heat is generated. A paper entitled, HEATING AROUND INTRAVASCULAR GUIDEWIRES BY RESONATING RF WAVES by Konings, et al., journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the leads of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar, multipolar and the like. It is very important that excessive RF current not flow at the interface between the lead distal tip electrode or electrodes and body tissue. In a typical cardiac pacemaker, for example, the distal tip electrode can be passive or of a screw-in helix type as will be more fully described. In any event, it is very important that excessive RF current not flow at this junction between the distal tip electrode and, for example, into surrounding cardiac or nerve tissue. Excessive current at the distal electrode to tissue interface can cause excessive heating to the point where tissue ablation or even perforation can occur. This can be life-threatening for cardiac patients.

For neurostimulator patients, such as deep brain stimulator patients, thermal injury can cause permanent disability or even be life threatening. Similar issues exist for spinal cord stimulator patients, cochlear implant patients and the like.

A very important and possibly life-saving solution is to be able to control overheating of implanted leads during an MRI procedure. A novel and very effective approach to this is to first install parallel resonant inductor and capacitor bandstop filters at or near the distal electrode of implanted leads. For cardiac pacemaker, these are typically known as the tip and ring electrodes. One is referred to U.S. Pat. Nos. 7,363,090; 7,945,322; 7,853,324; US 2008/0049376 A1; U.S. Pat. Nos. 7,511,921; 7,899,551; and 7,853,325A1, the contents of all of which are incorporated herein. U.S. Pat. No. 7,945,322 relates generally to L-C bandstop filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals.

Other types of component networks may also be used in implantable leads to raise their impedance at MRI frequencies. For example, a series inductor may be used as a single element low pass filter. The inductance will tend to look like a high impedance at high frequencies, such as the RF pulsed frequencies of a typical MRI scanner. For more information on this refer to U.S. Pat. No. 5,217,010 (Tsitlik et al.), the contents of which are incorporated herein by reference.

U.S. Pat. Nos. 7,363,090 and 7,945,322 show resonant L-C bandstop filters placed at the distal tip and/or at various locations along the medical device leads or circuits. These L-C bandstop filters inhibit or prevent current from circulating at selected frequencies of the medical therapeutic device. For example, for an MRI system operating at 1.5 Tesla, the pulsed RF frequency is 63.84 MHz, as described by the Lamour Equation for hydrogen. The L-C bandstop filter can be designed to resonate at or near 63.84 MHz and thus create a high impedance (ideally an open circuit) in the lead system at that selected frequency. For example, the L-C bandstop filter when placed at the distal tip electrode of a pacemaker lead will significantly reduce RF currents from flowing through the distal tip electrode and into body tissue. The L-C bandstop filter also reduces EMI from flowing in the leads of a pacemaker thereby providing added EMI protection to sensitive electronic circuits. In general, the problem associated with implanted leads is minimized when there is a bandstop filter placed at or adjacent to or within its distal tip electrodes.

At high RF frequencies, an implanted lead acts very much like an antenna and a transmission line. An inductance element disposed in the lead will change its transmission line characteristics. The inductance can act as its own antenna pick-up mechanism in the lead and therefore, ideally, should be shielded. When one creates a very high impedance at the distal electrode to tissue interface by installation of a resonant bandstop filter as described in U.S. Pat. No. 7,038,900 and as further described in U.S. Pat. No. 7,945,322, there is created an almost open circuit which is the equivalent of an unterminated transmission line. This causes a reflection of MRI induced RF energy back towards the proximal end where the AIMD (for example, a pacemaker) is connected. In order to completely control the induced energy in an implanted lead, one must take a system approach. In particular, a methodology is needed whereby energy can be dissipated from the lead system at the proximal end in a way that does not cause overheating either at the distal electrode interface or at the proximal end cap. Maximizing energy transfer from an implanted lead is more thoroughly described in US 2010/0160997 A1, the contents of which are incorporated herein by reference.

In order to work reliably, leads need to be stably located adjacent to the tissue to be stimulated or monitored. One common mechanism for accomplishing this has been the use of a fixation helix, which exits the distal end of the lead and is screwed directly into the body tissue. The helix itself may serve as an electrode or it may serve as an anchoring mechanism to fix the position of an electrode mounted to, or forming a portion of the lead itself.

A problem associated with implanted leads is that they act as an antenna and tend to pick up stray electromagnetic signals from the surrounding environment. This is particularly problematic in an MRI environment, where the currents which are imposed on the leads can cause the leads to heat to the point where tissue damage is likely. Moreover, the currents developed in the leads during an MRI procedure can damage the sensitive electronics within the implantable medical device. Bandstop filters, such as those described in U.S. Pat. No. 7,363,090 and US 2011/0144734 A1, reduce or eliminate the transmission of damaging frequencies along the leads while allowing the desired frequencies to pass efficiently through. Referring to U.S. Pat. No. 7,363,090, one can see that a simple L-C bandstop filter can be realized using discrete passive electronic components. This involves installing a capacitor in parallel with an inductor. As stated in U.S. Pat. No. 7,363,090 column 19, lines 59-65, "It is also possible to use a single inductive component that has significant parasitic capacitance between its adjacent turns. A careful designer using multiple turns could create enough parasitic capacitance such that the coil becomes self-resonant at a predetermined frequency. In this case, the predetermined frequency would be the MRI pulsed frequency."

Several patents describe methods of constructing leads either with inductance or with inductance that has parasitic capacitance that forms bandstop filters. These include U.S. Pat. Nos. 5,217,010 and 7,561,906. Other publications that describe inductive structures wherein parasitic capacitors form bandstop filters are US 2006/0041294, US 2008/0243218, U.S. Pat. No. 7,917,213, US 2010/0174348, US 2010/0318164, US 2011/0015713, US 2009/0281592, and US 2003/0144720.

Accordingly, there is a need for attenuating the RF energy that can be induced onto or into an implanted lead system. Moreover, there is a need for an implantable medical lead where the novel multilayer helical wave filter design presents a high impedance at MRI RF pulsed frequencies and thereby prevents dangerous overheating of the leads and/or its distal electrodes that are in contact with body tissue. The present invention fulfills these needs and provides other related advantages.

SUMMARY OF THE INVENTION

The multilayer helical wave filter of the present invention has a primary resonance at a selected RF therapeutic or diagnostic frequency or frequency range and comprises an elongated conductor which may form at least a portion of an implantable medical lead. At resonance, the multilayer helical wave filter provides a very high impedance at its resonance frequency or frequencies. In this regard, even though its equivalent circuit is more complex, the multilayer helical wave filter of the present invention performs in a similar manner to that of a simple bandstop filter consisting of a capacitor in parallel with an inductor. The elongated conductor that forms the multilayer helical wave filter has at least one planar surface and includes a first helically wound segment having a first end and a second end which forms a first inductive component, a second helically wound segment having a first end and a second end which forms a second inductive component, and a third return connecting segment which extends substantially the length of the first and second helically wound segments to connect the second end of the first helically wound segment to the first end of the second helically wound segment. The first and second helically wound segments are wound in the same longitudinal direction and share a common longitudinal axis. The at least one planar surface of the first helically wound segment faces the at least one planar surface of the second helically wound segment, and a dielectric material is disposed between the facing planar surfaces of the first and second helically wound segments and between adjacent coils of the first and second helically wound segments. Importantly, the direction of RF current flow will be the same in both the first and second helically wound segments.

In preferred embodiments, the multilayer helical wave filters, which consist of first and second helically wound segments, are disposed at or adjacent to or within one or more distal electrodes. The electrode may comprise the electrodes of cardiac pacemakers, such as a tip or a ring electrode, and may be active (helix screw-in) or passive. Furthermore, the electrodes could be neurostimulator electrodes, including electrode probe bundles, pad electrodes, ring electrodes, nerve cuff electrodes, or the like.

Inductances created by the inductive components are electrically disposed in parallel with parasitic capacitance between the first and the second helically wound segments. Further, inductance formed by the inductive components is electrically disposed in parallel with parasitic capacitance between facing planar surfaces of the first and second helically wound segments.

The elongated conductor may comprise a rectangular or a square cross-sectional configuration. The dielectric material may comprise a polyimide, a liquid crystal polymer, PTFE, PEEK, ETFE, PFA, FEP, parylene, a dielectric polymer material, or titanium oxide. It is not necessary to use only one dielectric type. In fact, an advantage of the present invention is that different dielectric materials may be used in different areas of the multilayer helical wave filter. For example, one could use one type of dielectric with a specific dielectric constant, for a portion between the first and second helically wound segments, a second dielectric with a different dielectric constant in another portion and even a third dielectric in different portion. This would change the parasitic capacitance and the resonant characteristics of the various sections of the multilayer helical wave filter. In other words, the multilayer helical wave filter could be designed to be resonant at a number of frequencies corresponding to various MRI RF pulsed frequencies and/or their harmonics.

The return connecting segment may extend inside of both the first and second helically wound segments, or the return connecting segment may extend exteriorly of both the first helically wound and second helically wound segments. Further, the connecting segment may be coiled and again routed either exteriorly of the first and second helically wound segments, or inside of both the first and second helically wound segments. The return connecting segment may be straight or curvilinear. Since the induced RF current is reversed in the return segment, it is important that the return connecting segment not be extended between the first helically wound segment and the second helically wound segment.

In various embodiments, one of the helically wound segments is disposed radially inside the other, or the first and second helically wound segments are co-radially disposed about the common longitudinal axis in a side-by-side relationship.

In another embodiment, a third helically wound segment has a first end and a second end and forms a third inductive component. The first, second and third helically wound segments are wound in the same longitudinal direction, wherein a planar surface of the third helically wound segment faces a planar surface of the second helically wound segment. The elongated conductor includes a second connecting segment extending substantially the length of the second and third helically wound segments to connect the second end of the second helically wound segment to the first end of the third helically wound segment. A dielectric material is disposed between facing planar surfaces of the second and third helically wound segments.

In yet another embodiment of the multilayer helical wave filter of the present invention, a second elongated conductor is provided, which has at least one planar surface and comprises (1) a first helically wound segment having a first end and a second end and forming a first inductive component, (2) a second helically wound segment having a first end and a second end and forming a second inductive component, and (3) a return connecting segment extending substantially the length of the first and second helically wound segments to connect the second end of the first helically wound segment to the first end of the second helically wound segment. The first and second helically wound segments are wound in the same longitudinal direction and share a common longitudinal axis, wherein the at least one planar surface of the first helically wound segment faces the at least one planar surface of the second helically wound segment. The return connecting segment provides that current paths in first and second helically wound segments will be in the same direction. One or more dielectric materials are disposed between the facing planar surfaces of the first and second helically wound segments, and between adjacent coils of the first and second helically wound segments. This second elongated conductor provides that the wave filter has both a first and a secondary primary resonance at selected MRI pulsed frequencies or frequency ranges.

The inductance created by the inductive components of the second elongated conductor is electrically disposed in parallel with parasitic capacitance between the first and the second helically wound segments. Moreover, the inductance formed by the inductive components of the second elongated conductor is electrically disposed in parallel with parasitic capacitance between facing planar surfaces of the first and second helically wound segments.

The elongated conductors are wound in the same longitudinal direction and share the same longitudinal axis, which means that the RF current paths in the elongated conductors of all helically wound segments are in the same direction. The second elongated conductor further comprises a rectangular or a square cross-sectional configuration.

The return connecting segment of the second elongated conductor extends within or exteriorly of both the first helically wound segment and the second helically wound segment. The return connecting segment of the second elongated conductor may further be coiled exteriorly or interiorly of both the first and second helically wound segments.

In various configurations, one of the helically wound segments of the second elongated conductor may be disposed radially inside the other, or the first and second helically wound segments of the second elongated conductor may be co-radially disposed about the common longitudinal axis in a side-by-side relationship. One may also vary the pitch of the helical winding of the first segment and/or the pitch of the second segment in order to vary the inductance and parasitic capacitance. By varying the pitch along the length of the multilayer helical wave filter, one can create multiple resonances. For example, one could create a resonance at the RF pulsed frequency of a 1.5 Tesla MRI scanner and also a second or even third resonance at its harmonics at 128 and 192 MHz.

Preferably, the multilayer helical wave filter has a Q at resonance wherein the resultant 10 dB bandwidth is at least 10 KHz. In various embodiments, the Q at resonance may be at least 100 KHz and in other embodiments at least 0.5 MHz. By controlling the dielectric type, the dielectric constant of the dielectric material may be varied from 2 to 50.

The primary resonance of the wave filter may comprise a plurality of selective MRI RF pulsed frequencies or frequency ranges, and the wave filter may resonate at the selected RF frequency or frequency range and also at one or more of its harmonic frequencies.

The first helically wound segment may have a different cross-sectional area than the second helically wound segment. Moreover, the first helically wound segment may have a different number of turns than the second helically wound segment.

Electric insulation is typically provided for attenuating RF currents and body fluids or tissues from degrading the impedance of the wave filter at resonance. The insulation is typically continuous with an overall insulation of the implantable medical lead, and may include an insulative sleeve disposed about the elongated conductor.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 35 is a sectional view taken generally along line 35-35 from FIG. 34;

FIG. 36 is an electrical schematic illustration of the structure shown in FIGS. 34 and 35;

DETAILED DESCRIPTION OF THE PREFERRED EMBODIMENTS

Figure 1:
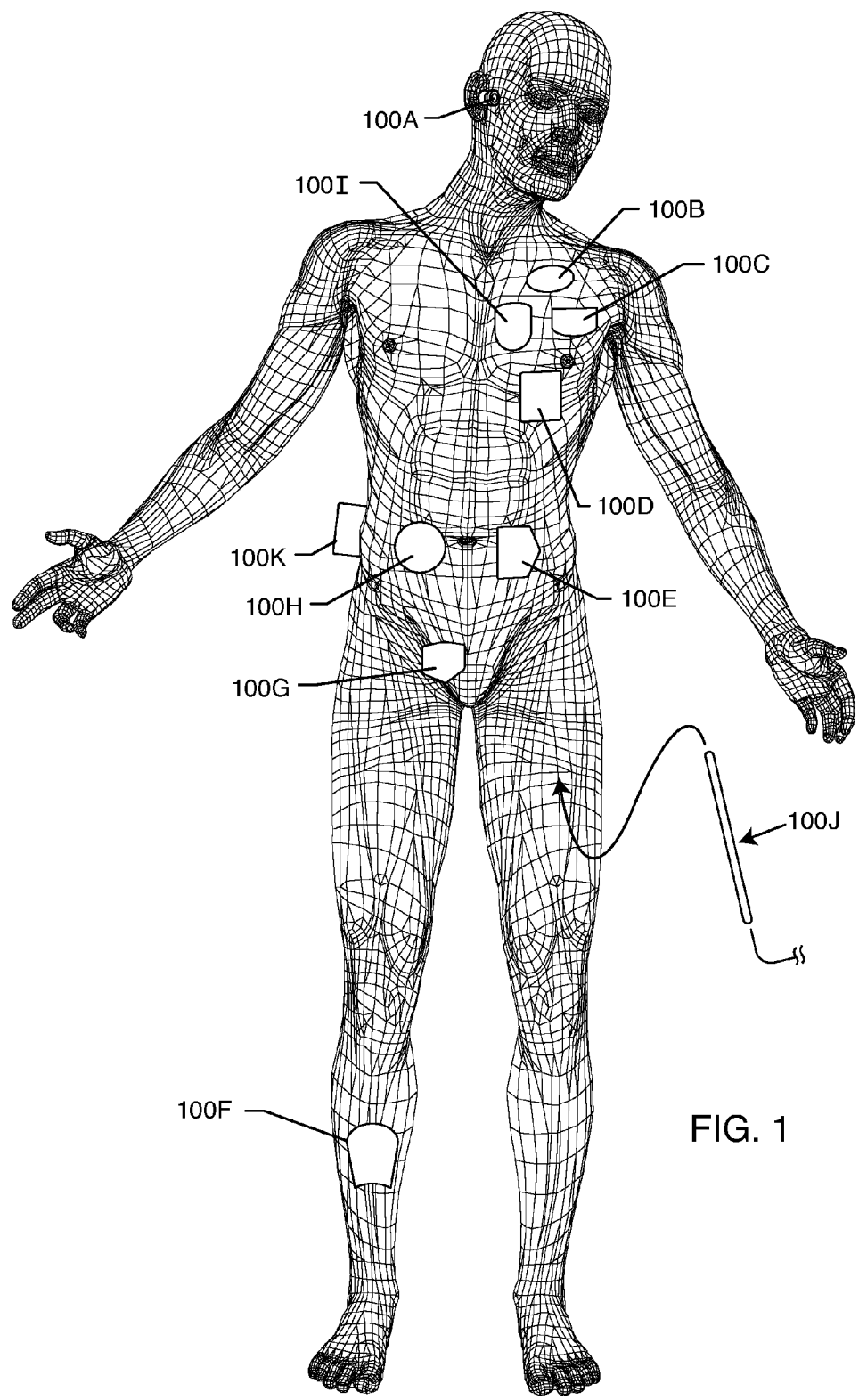
FIG. 1 is a wire-formed diagram of a generic human body showing a number of exemplary active medical devices (AMDs)

As shown in the drawings for purposes of illustration, the present invention relates to multilayer helical wave filters placed between proximal and distal ends of an implantable lead of an active medical device (AMD). One or more multilayer helical wave filters may be implanted anywhere along the length of implanted leads or electrodes of AMDs. In particular, the multilayer helical wave filter of the present invention presents a very high impedance (which impedes RF current flow) at one or more MRI RF pulsed frequencies. The present invention is particularly important to protect implanted leads from overheating in the presence of high power electromagnetic field environments, such as the RF pulsed fields produced by a clinical MRI scanner. In a broad sense, the present invention comprises a multilayer helical wave filter which is installed in one or more locations along the length of the conductors of an implanted lead. As will be shown, it is also very important that the multilayer helical wave filter be insulated along its entire length with insulation integral to the implanted lead so that RF leakage paths do not occur around the filter through ionic body fluids.

The multilayer helical wave filter of the present invention acts as an impeding circuit. The operation of impeding circuits and diversion circuits is more thoroughly described in U.S. Pat. No. 7,751,903 and US 2010/0160997 A1, which are incorporated herein by reference. In a particularly preferred embodiment, the multilayer helical wave filter has a Q and 3-dB bandwidth such that, at resonance, it offers attenuation of at least 10-dB over a range of MRI RF pulsed frequencies at least 10 kHz wide, and more preferably at least 100 kHz or even on the order of MHz. The novel multilayer helical wave filter of the present invention can be used in combination with any of the diversion circuits as described in U.S. Pat. No. 7,751,903 and US 2010/0160997 A1.

In the case where a multilayer helical wave filter is installed at or near the distal electrode of an implanted lead, the RF energy induced by the MRI pulse field is inhibited from flowing into body tissues. However, even when a distal electrode multilayer helical wave filter is used, the induced RF energy still resides in the lead system. In other words, by preventing this induced energy from flowing to sensitive tissues at distal electrode interfaces, a great deal has been accomplished; however, it is still important to carefully dissipate the remaining energy that is trapped in the lead system. Dissipation of the RF energy that's reflected off of a distal tip electrode filter is more thoroughly described in US 2010/0217262 A1 which is incorporated herein by reference. US 2010/0217262 reference teaches how to dissipate energy to the relatively large surface area of the AIMD housing thereby safely removing it from the lead system.

FIG. 1 is a wire formed diagram of a generic human body showing a number of exemplary implantable medical devices. 100A is a family of implantable hearing devices which can include the group of cochlear implants, piezoelectric sound bridge transducers and the like. 100B includes an entire variety of neurostimulators and brain stimulators. 100C shows a cardiac pacemaker. 100D includes the family of left ventricular assist devices (LVAD's) and artificial hearts. 100E includes an entire family of drug pumps which can be used for dispensing of insulin, chemotherapy drugs, pain medications and the like. 100F includes a variety of implantable bone growth stimulators for rapid healing of fractures. 100G includes urinary incontinence devices. 100H includes the family of pain relief spinal cord stimulators and anti-tremor stimulators. 100I includes a family of implantable cardioverter defibrillator (ICD) devices, congestive heart failure devices (CHF), and cardio resynchronization therapy devices, otherwise known as CRT devices. 100j illustrates a family of probes or catheters that can be transvenously inserted during catheter lab procedures. These are normally considered short-term implants in that they are inserted within the human body for at most a few hours. 100K is an externally worn active medical device, such as a neurostimulator. It can be worn on a belt, placed in a pocket or the like. Typically, it has one or more implanted leads. 100K also represents an externally worn drug pump or the like.

The various types of active medical devices (AMDs) illustrated in FIG. 1 generally represent any type of AMD that is either a "long-term" or "short-term" implant. "Short-term" implants include AMDs like probes or catheters or surgical devices that are "short-term" body insertions used either for diagnostic or therapy delivery purposes. For example, a probe or catheter is typically used in a cath-lab situation wherein it is temporarily inserted through a femoral (or other) artery where the entire procedure lasts minutes or at most a few hours. On the other hand, a long-term implant, such as a cardiac pacemaker, is generally designed to be implanted in the human body for many years. There are significant differences in the art between a short-term and a long-term implant. For example, for a long-term implant, one has to worry greatly about the long-term biocompatibility, toxicity and even the hermeticity of the implant. In contrast, a probe, catheter or temporary loop recorder need only operate or be reliable for a matter of minutes or even hours. In general, a short-term implant is often considered to be a disposable device. In addition, the FDA regulatory approval processes for long-term implants is significantly different and involves much more rigorous testing and product safety and reliability criteria. The FDA Center for Devices and Radiological Health (FDA-CDRH) is the responsible regulatory agency for long-term active cardiac implants. As used herein, the term active medical device (AMD) or active implantable medical device (AIMD) is construed to include long-term implants and also short-term body insertions, such as probes or catheters. The term AMD is inclusive of active implantable medical devices (AIMDs) and also externally worn medical devices that are associated with an implanted lead.

Throughout, the term lead generally refers to implantable leads and their conductors that are external to the housing of the active medical device. These leads tend to have a proximal end, which is at or adjacent to the AMD, and a distal end, which typically includes one or more electrodes which are in contact with body tissue.

Figure 2:
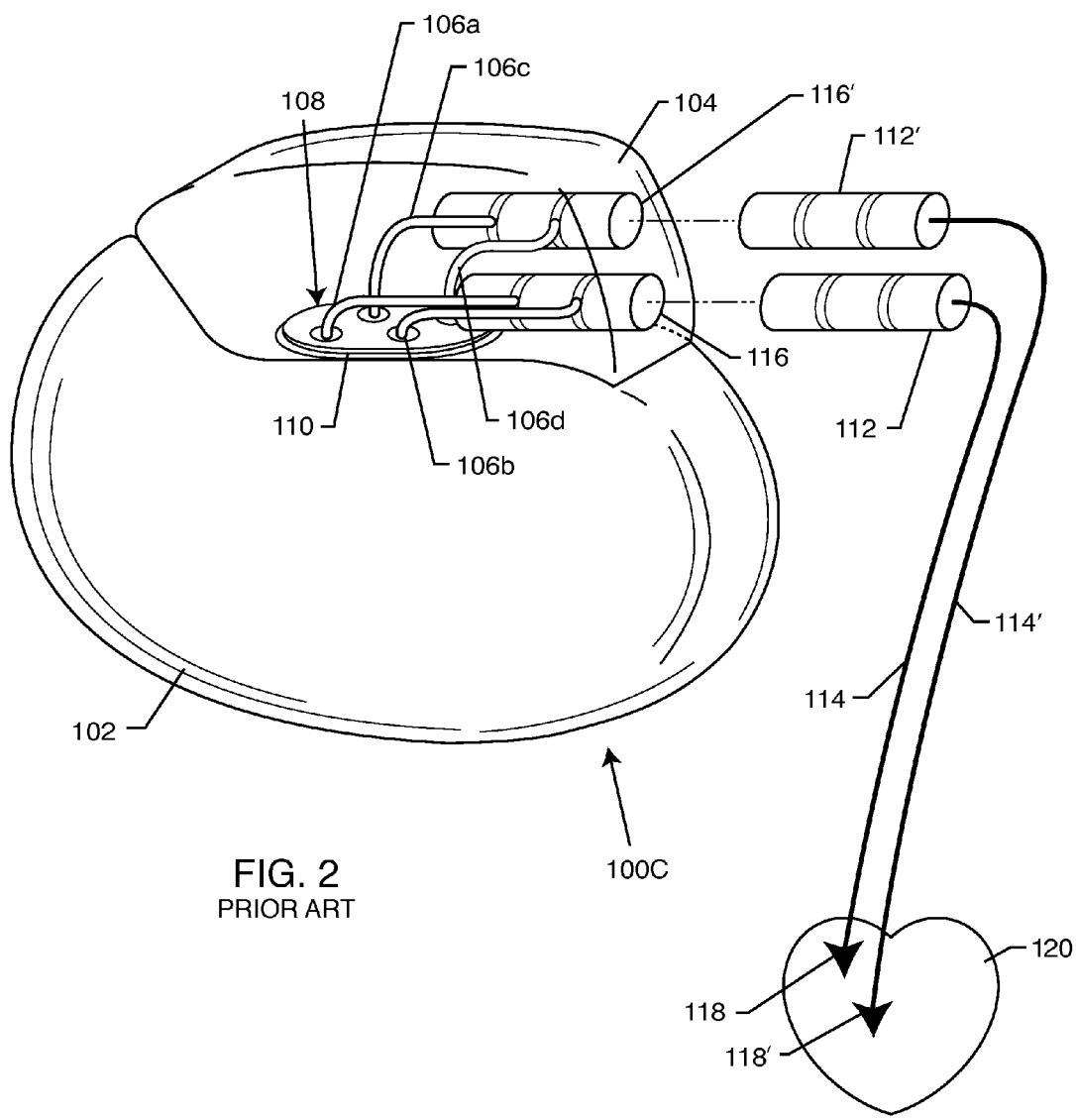
FIG. 2 illustrates an exemplary prior art cardiac pacemaker with the leads schematically shown extending to a patient's heart.

FIG. 2 is a drawing of a typical cardiac pacemaker 100C showing a titanium case or housing 102 and an IS-1 header connector block 104. The titanium case or housing 102 is hermetically sealed, however there is a point where leadwires 106a-106d must ingress and egress a hermetic seal. This is accomplished by providing a hermetic terminal assembly 108 that generally consists of a ferrule 110 which is laser welded to the titanium housing 102 of the pacemaker 100C.

Four leadwires are shown consisting of leadwire pair 106a and 106b and leadwire pair 106c and 106d. This is typical of what is known as a dual chamber bipolar cardiac pacemaker. The IS-1 connectors 112 and 112' of leads 114 and 114' are designed to plug into receptacles 116 and 116' in the header block 104. The receptacles 116 and 116' are low voltage (pacemaker) connectors covered by an ANSI/AAMI ISO standard IS-1. Higher voltage devices, such as implantable cardioverter defibrillators (ICDs), are covered by ANSI/AAMI ISO standard DF-1. A new standard which will integrate both high voltage and low voltage connectors into a miniature in-line quadripolar connector is known as the IS-4 series. The implanted leads 114 and 114' are typically routed transvenously in a pacemaker application down into the right atrium 118 and the right ventricle 118' of the heart 120. New generation biventricular or CRT-P devices may introduce leads to the outside of the left ventricle, which devices have proven to be very effective in cardiac resynchronization and treating congestive heart failure (CHF).

Although the present invention will be described herein in the context and environment of a cardiac pacemaker 100C and its associated leads 114 and 114', the present invention may also be advantageously utilized in many other types of AMDs as briefly outlined above and shown in FIG. 1, as well as in other commercial electronic, military, aerospace and other applications. In the following discussion, to the extent practicable, functionally equivalent components will retain the same or a similar reference number, irrespective of the particular embodiment being described.

Figure 3:
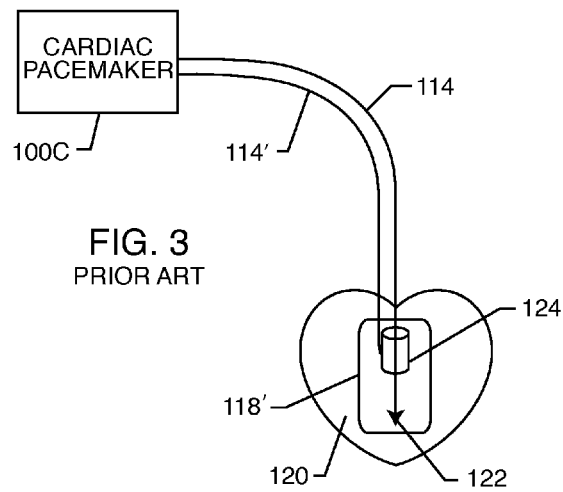
FIG. 3 is a schematic illustration of a prior art AMD with a bipolar lead.

FIG. 3 illustrates a prior art single chamber bipolar AMD 100C and lead system 114 and 114' with a distal tip electrode 122 and a ring electrode 124 typically as used with a cardiac pacemaker 100C. Should the patient be exposed to the fields of an MRI scanner or other powerful emitter used during a medical diagnostic procedure, currents that are directly induced in the lead system 114, 114' can cause heating by $I^2R$ losses in the lead system or by heating caused by RF current flowing from the tip and ring electrodes 122, 124 into body tissue. If these induced RF currents become excessive, the associated heating can cause damage or even destructive ablation to body tissue.

Figure 4:
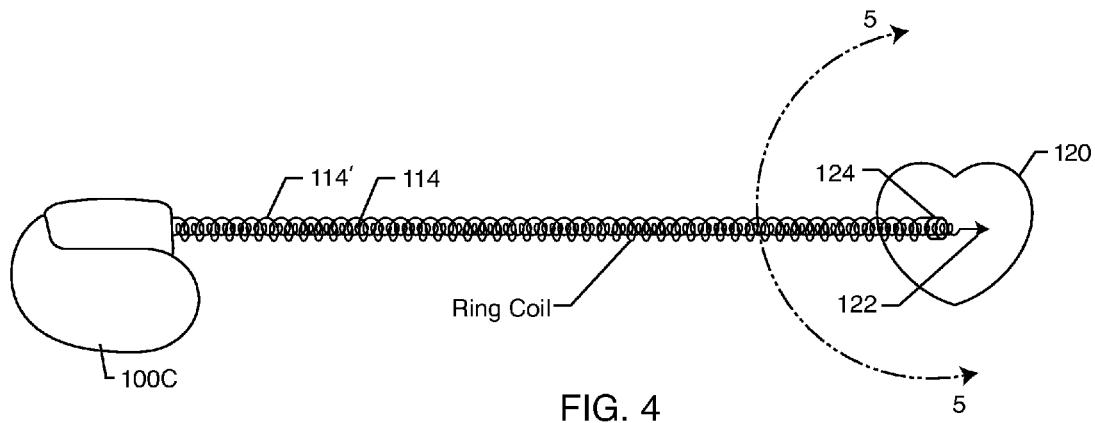
FIG. 4 is similar to FIG. 3, except that the bipolar lead wires are coaxially wound around one another.

FIG. 4 illustrates a single chamber bipolar cardiac pacemaker 100C, and leads 114 and 114' having distal tip 122 and distal ring 124 electrodes. This is a spiral wound (coaxial) system where the ring coil 114' is wrapped around the tip coil 114. There are other types of pacemaker leadwire systems in which these two leads lay parallel to one another (known as a bifilar lead system), which are not shown.

Figure 5:
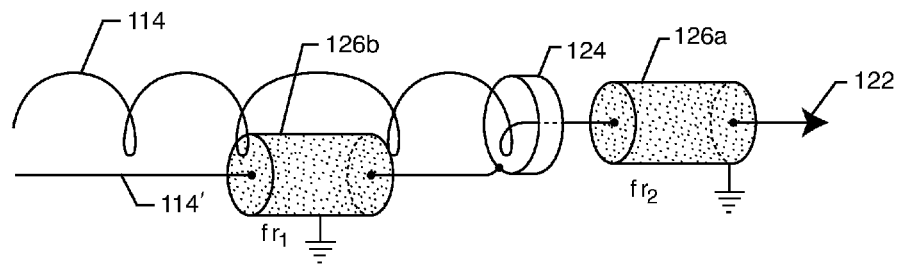
FIG. 5 is an enlarged view of the area indicated by line 5-5 from FIG. 4, illustrating wave filters associated with both the tip and ring electrodes.

FIG. 5 is taken from section 5-5 of FIG. 4, and shows multilayer helical wave filters 126a and 126b. As illustrated, there is a multilayer helical wave filter 126a of the present invention at or adjacent to the tip electrode 122 also a multilayer helical wave filter 126b at the ring electrode 124. In general, the multilayer helical wave filters 126, would be tuned to be resonant at a center frequency in a range of MRI RF pulsed frequencies. The operation of simple L-C bandstop filters in implanted leads is more thoroughly described by U.S. Pat. Nos. 7,363,090 and 7,945,322. The performance of the multilayer helical wave filter 126 of the present invention is similar to that of a simple L-C bandstop filter, except that its equivalent circuit diagram is much more complicated. In addition, unlike a simple L-C bandstop filter, the multilayer helical wave filter can be designed with multiple resonances as described herein. It is useful to think of these multiple resonances as equivalent to multiple bandstop filters of varying resonant frequencies that are disposed in series with the implanted lead.

Figure 6:
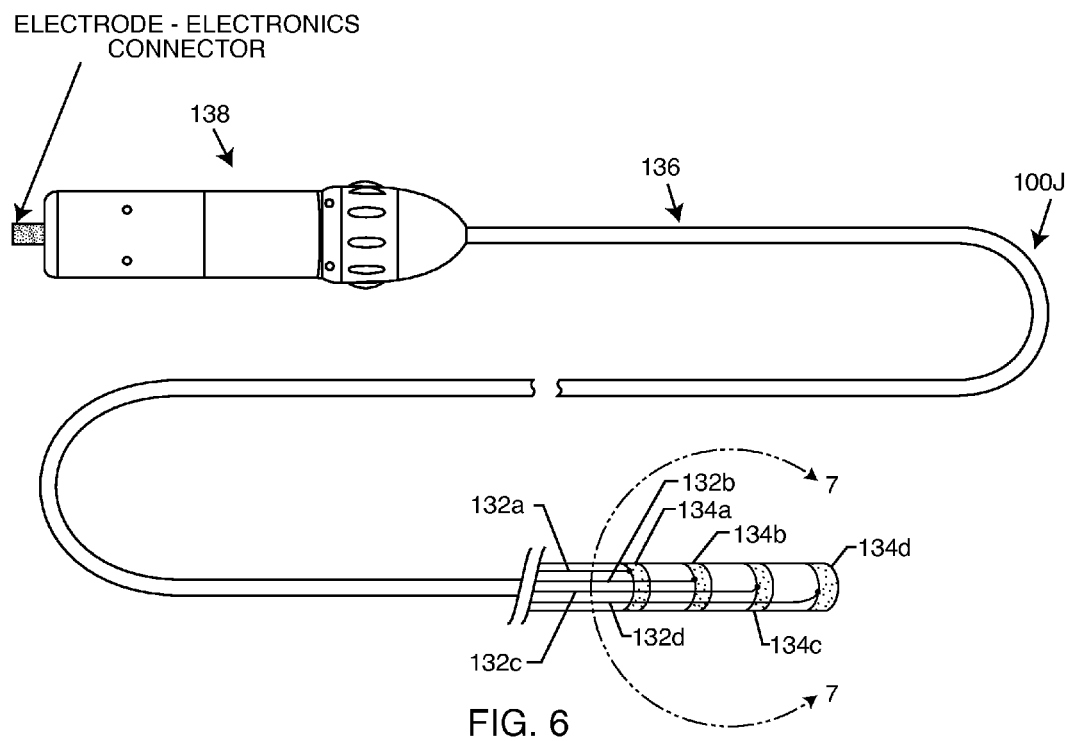
FIG. 6 illustrates a probe or catheter which has four distal electrodes.

FIG. 6 illustrates a probe or a catheter 100j which has four internal conductors 132a-132d which are directed to four different distal electrodes 134a-134d at its distal end. In the art, electrode 134d would be known as an ablation electrode wherein the other electrodes could be used for cardiac electrical mapping and the like. The probe or catheter 100j encompasses multilayer helical wave filters 126a-126d of the present invention in series with each of the conductors that are directed to the electrodes 134a-134d. The probe or catheter 100j consists of a flexible and steerable probe or catheter section 136 which may be bent as shown and generally terminates in the distal electrodes 134a-134d. There is generally a catheter handle or body 138 which is used for steering the probe or catheter into the body transvenously. These handles can take the form of a pistol grip or many other shapes.

Figure 7:
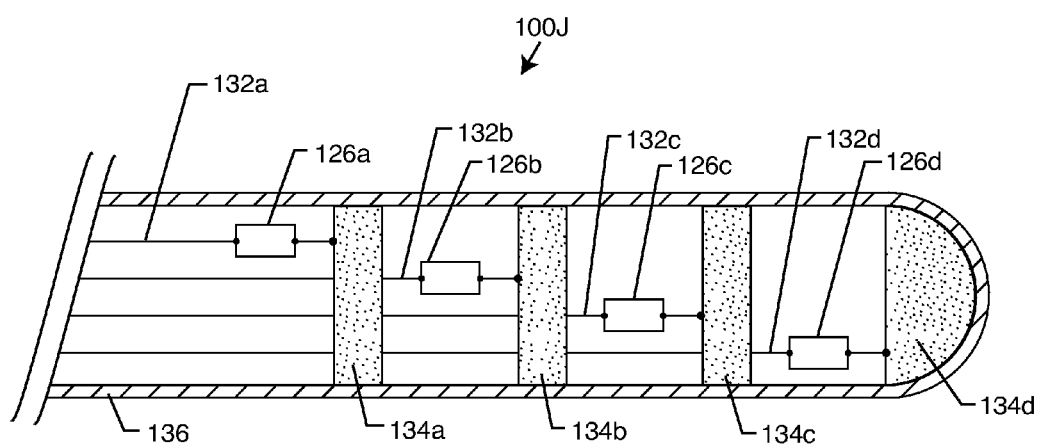
FIG. 7 is an enlarged view of the distal tip section of the probe or catheter of FIG. 6.

FIG. 7 is a sectional view taken generally along section 7-7 from FIG. 6. Shown are the four conductors 132a-132d which are housed inside the probe or catheter steerable body 136. There are four multilayer helical wave filter 126a-126d in accordance with the present invention. Each of these multilayer helical wave filters 126 is in series with one of the distal electrodes 134. These multilayer helical wave filters 126 impede MRI RF induced currents from flowing into the electrodes 134 and thereby inadvertently overheating and damaging adjacent living tissues.

Figure 8:
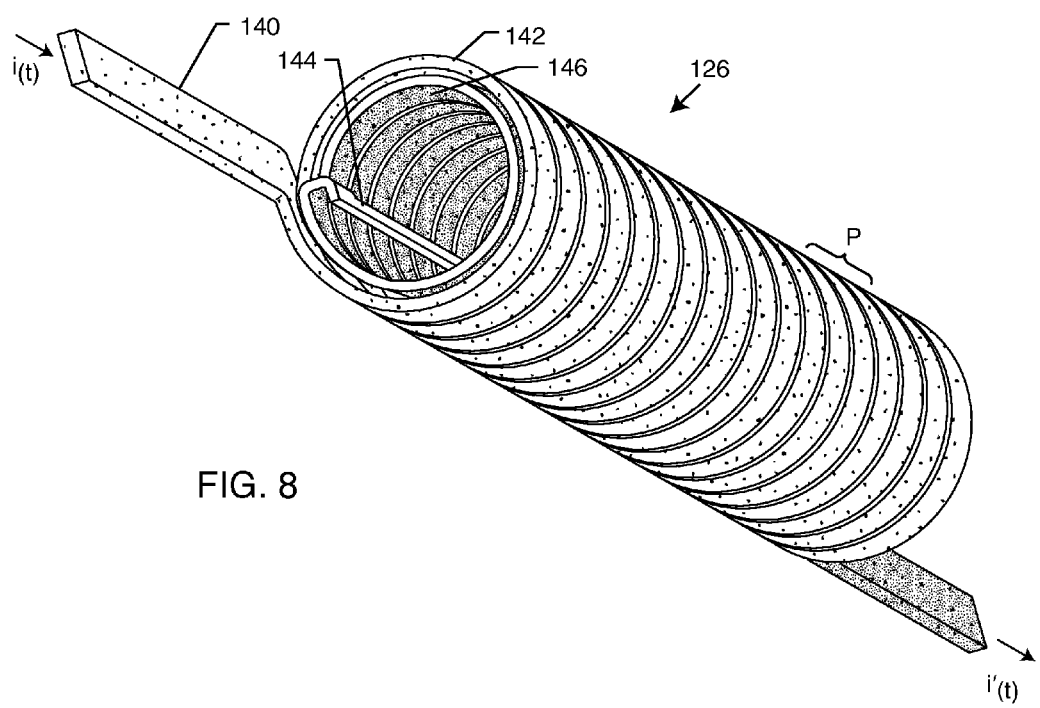
FIG. 8 is an isometric view of a multilayer helical wave filter embodying the present invention.

FIG. 8 is an isometric view of a multilayer helical wave filter 126 of the present invention which is in series with an implanted lead (not shown). Also not shown is an overall insulation covering the multilayer helical wave filter which is contiguous with the implanted lead to provide isolation of the multilayer helical wave filter from body fluids. This insulation is omitted for clarity purposes in many of the drawings, however, it will be understood that this insulation is essential so that the impedance of the multilayer helical wave filter at resonance is not degraded by parallel RF current paths through body tissues. Shown is an elongated rectangular conductor 140 with an MRI RF induced current $i_{(t)}$ shown entering it. The elongated conductor 140 forms a first helically wound inductor segment 142. Then there is a return wire connecting segment 144 (which could be coiled) which is used to wind a second helically wound inductor 146 inside of the first segment. Accordingly, the first helically wound inductor segment 142 and the second helically wound inductor segment 146 are wound in the same longitudinal direction and share a common longitudinal axis where planar surfaces of the first helically wound segment 142 face or abut planar surfaces of the second helically wound inductor segment 146. In general, the elongated conductor has a dielectric insulation which may also be used to insulate the entire multilayer helical wave filter such that RF current through body fluids do not degrade its impedance at resonance. A capacitance is therefore formed between the planar surfaces of the first helically wound inductor segment 142 and the second helically wound inductor segment 146. There is also a capacitance that is formed between adjacent turns. The effect of these inductor segments and capacitances will be to form a helical wave filter 126 in accordance with the present invention. There are a number of advantages to the multilayer helical wave filter construction as illustrated in FIG. 8. First of all, by using biocompatible materials, there is no need for discrete components placed inside of a hermetic seal. One is referred to US 2010/0231237 for a description of how discrete passive capacitors and inductors are placed inside a hermetically sealed housing to form a bandstop filter. This package is both large and very expensive to produce. It will be apparent that the multilayer helical wave filter 126 of the present invention is both volumetrically efficient and relatively much lower in cost.

Figure 9:
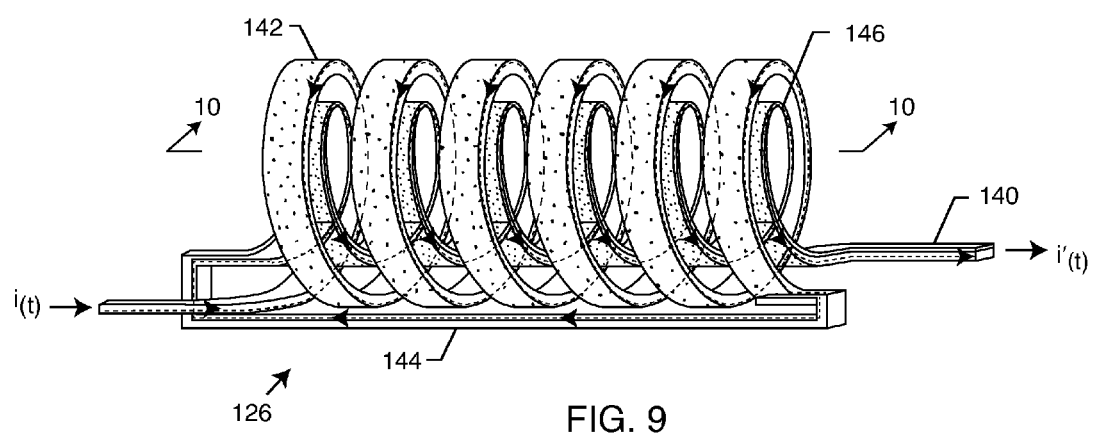
FIG. 9 is a partially schematic view of the structure shown in FIG. 8, wherein the first helically wound segment is much larger in diameter than the second helically wound segment for illustrative purposes.

FIG. 9 is very similar to FIG. 8 except that the first helically wound segment 142 is much larger in diameter than the second helically wound inductor segment 146. This is to better illustrate the principles of the present invention and also indicate the direction of current flow. As one can see, in both the first (outer) helical wound inductor segment 142 and the second (inner) helically wound inductor segment 146, the RF induced current flow from MRI is always in the same direction. Having the current flow be in the same direction of the various inductor segments of the present invention is critically important and a major distinguishing feature over the prior art. Having the RF current flow in the same direction increases the inductance by up to a factor of four times as compared to having a single inductor winding. Current flow in the same direction results in much stronger effective fields as opposed to field reduction in the case of opposite current flows in adjacent turns. The design of the return wire or segment 144, which can be straight, curvilinear or coiled, (and also be either external or internal to the inductor segments) is a key. In the prior art, which teaches parasitic inductance to form simple bandstop filters, the current flow of adjacent coils is generally in opposite directions (reference Bottomley US 2008/0243218 A1). In the present invention, the fields associated with the return wire or segments 144 are negligible in comparison with the fields generated by both the inner and outer multilayer helical inductor segments 142 and 146.

Referring once again to FIG. 8, one could also vary the pitch between adjacent turns of portions of the multilayer helical wound wave filter 126. This would create sections that had a different resonant frequency as compared to other sections. Accordingly, it is a feature of the present invention that the multilayer helical wave filter 126 can be resonant at 1, 2 or even "n" number of selected RF frequencies. Similar effects can be achieved by carefully controlling the overlap area between the planar surfaces of the outer inductor segment 142 and the inner inductor segment 146. This would affect the amount of parasitic capacitance and hence the resonant frequency. It is also possible to control this parasitic capacitance by controlling the dielectric thickness or the dielectric type in various sections of the multilayer helical wave filter 126 of the present invention. By controlling the dielectric type, the dielectric constant can be varied anywhere from two to fifty. Most polymer-type dielectric coatings have a dielectric constant that fall between two and four. However, there are certain other types of dielectrics such as tantalum oxide, which would provide significantly higher dielectric constants (closer to 40). Different materials with different dielectric constants can be used in different sections of the multilayer helical wave filter.

In FIG. 8, one can see that the return wire or segment 144 is directed through the inside of both the first helically wound inductor segment 142 and the second helically wound inductor segment 146. FIG. 9 shows an alternate configuration wherein the return wire or segment 144 returns outside of both the first helically wound inductor segment 142 and the second helically wound inductor segment 146. In both FIG. 8 and FIG. 9, this return wire or connecting segment 144 is a straight elongated conductor. As will be shown in subsequent drawings, it will also be possible to coil this conductor 144 to increase mechanical flexibility of the filtered region. It is advised that the number of coils in this return path be limited to the minimum number of turns needed. This is to ensure that the eddy currents created by this return path (reverse currents) will be minimal and should not greatly impact the overall inductance of the first and second helical wound segments. Typically, the coiled return path is disposed at an angle to the first and second helically wound segments. This is to reduce the effect of eddy currents due to reverse currents in the return path [ideally close to 90 degrees is better but it could be anywhere greater than 0 degrees except (n*pi) n being 0, 1, 2, etc.]. This coiled return path is also useful in increasing or controlling the phase shift between the RF induced currents in the first helically wound inductor segment 142 relative to the currents in the second helically wound inductor segment 146.

Figure 10:
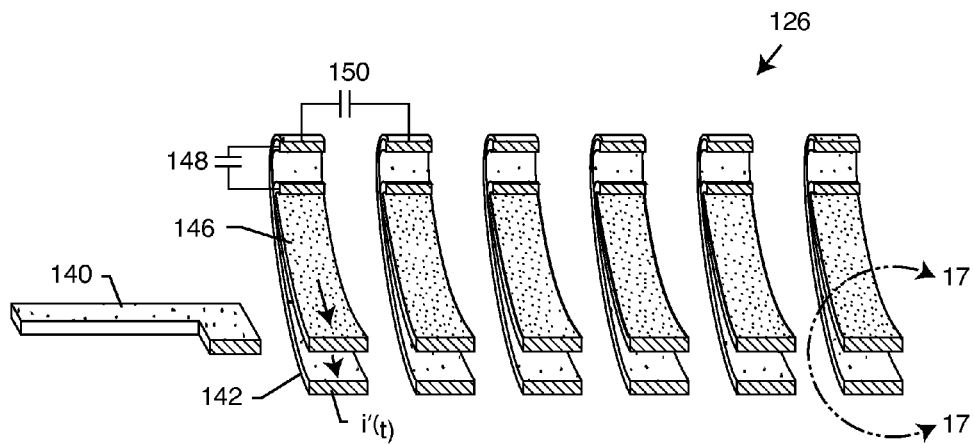
FIG. 10 is a sectional view taken generally along the line 10-10 from FIG. 9.

FIG. 10 is taken along section 10-10 from FIG. 9 and shows the elongated conductor 140 that forms the first helically wound inductor segment 142 and the second helically wound inductor segment 146 in cross-section. A capacitance 148 is formed between each of the coplanar surfaces between the first helically wound inductor 142 and the second helically wound inductor 146. In addition, there is a parasitic capacitance 150 that is formed between adjacent turns of both the first helically wound inductor 142 and the second helically wound inductor segments 146. The first helically wound inductor 142 and the second helically wound inductor 146 along with capacitance 148 and 150 form a multilayer helical wave filter in accordance with the present invention. By carefully adjusting the inductance and capacitance values, one can design the filter to resonate and provide a very high impedance at one or more selected MRI RF frequencies.

Figure 11:
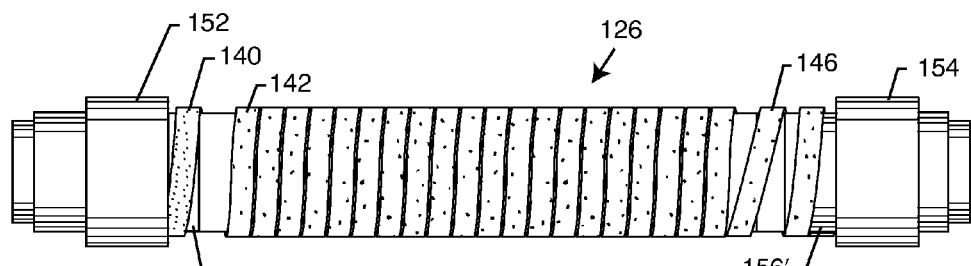
FIG. 11 is an elevational view of the multilayer helical wave filter of FIGS. 8 and 9 with end caps for convenient mechanical and electrical connection into an implantable lead.

FIG. 11 illustrates the multilayer helical wave filter previously illustrated in FIGS. 8 and 9 with end caps 152 and 154 for convenient mechanical and electrical connection in series into one or more conductors of an implantable lead of an AIMD. For example, an implantable lead 114 may be comprised of material MP35N. The lead conductor would be easily laser welded to mandrel end cap 156 of 152. The multilayer helical wave filter of the present invention is disposed between these two end caps. End cap 154 is shown connected to a distal electrode in contact with body tissues. The multilayer helical wave filter 126 of the present invention can be disposed anywhere along the length of an implanted lead. However, in a particularly preferred embodiment, it is disposed at or near the distal electrode. An electrode assembly (not shown) may be electrically and mechanically connected to end cap 154.

Figure 12:
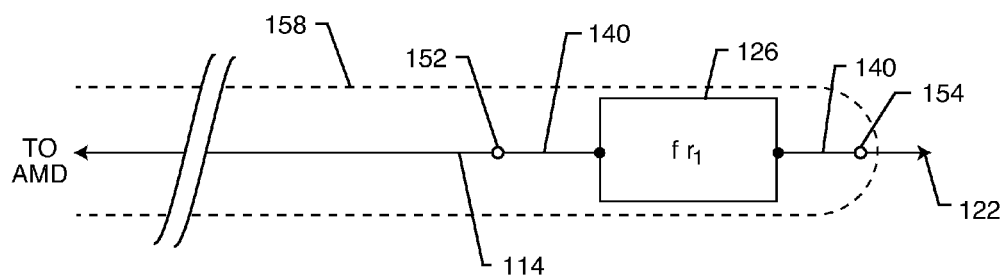
FIG. 12 is an electrical schematic diagram of the multilayer helical wave filter of FIG. 11.

FIG. 12 is a schematic diagram showing the multilayer helical wave filter 126 disposed between the two end caps 152 and 154. The end caps are shown attached in the implantable lead 114 with one end directed to the AMD and the other end directed to electrode 122. Multiple discrete multilayer helical wave filters may be installed in series anywhere along the length of the implanted lead as well. An overall electrical insulation 158 is integral to the lead 114 and also surrounds both end caps 152 and 154 in the entire multilayer helical wave filter 126. This insulation is very important to prevent RF electrical leakage through body fluids in parallel with the multilayer helical wave filter 126. Such RF leakage currents can significantly degrade the impedance of the multilayer helical wave filter at its one or more resonant frequencies. The amount of RF current leakage can be so severe that the multilayer helical wave filter becomes ineffective in preventing a distal electrode from overheating during an MRI scan.

Figure 13:
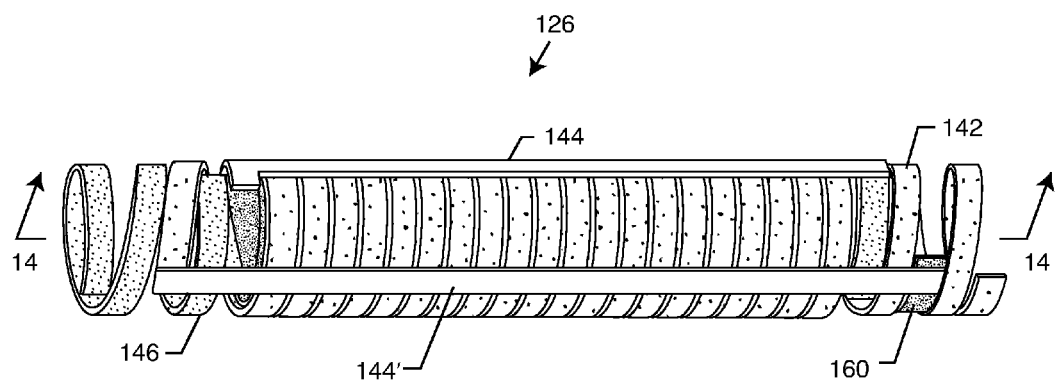
FIG. 13 is shows a structure similar to FIGS. 8-10, except that the multilayer helically wound wave filter includes a third helically wound inductor segment.

FIG. 13 is very similar to FIGS. 8, 9 and 10 except that it additionally has a third helically wound inductor segment 160. In this case, there are two return connecting segments 144 and 144'. All three of the helically wound inductor segments 142, 146 and 160 have facing planar surfaces in which capacitances 148 are formed. In addition, there are parasitic capacitances 150 between the turns of each one of the first, second and third helically wound inductor segments. The structure of FIG. 13 is useful to form multiple resonances to provide a high impedance and therefore a high degree of attenuation to various MRI RF pulsed frequencies. For example, typical 1.5 Tesla scanners operate at an RF pulsed frequency of approximately 64 MHz. 3.0 Tesla scanners are becoming more common and operate at 128 MHz RF pulsed frequency. By having a multilayer helical wave filter 126 that provides a resonance at both these frequencies, the implanted lead system can provide a high degree of immunity to overheating from both the 1.5 and 3-Tesla systems. Accordingly, the multilayer helical wave filter can be designed to be resonant at a first, second or even "n" selected RF frequencies.

Figure 14:
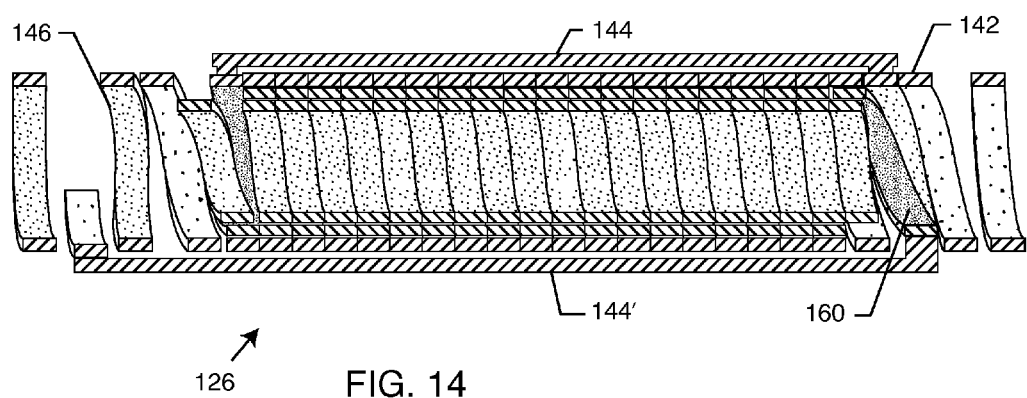
FIG. 14 is a sectional view taken generally along the line 14-14 from FIG. 13.

FIG. 14 is a sectional view taken from section 14-14 from FIG. 13. The three helically wound inductor segments 142, 146 and 160 are clearly shown. One could use the same dielectric material to coat all three helically wound segments or use different dielectric materials. For example, one could use one dielectric material between the first and second inductor segments and a second dielectric material between the second and third helically wound segments. This would create a different parasitic capacitance and thereby a different resonant frequency. The result is a multilayer helical wave filter 126 which could be designed to be resonant at a number of selected MRI RF pulsed frequencies. In general, the resonant frequency of each segment is approximated by the equation:

$$f_r = \frac{1}{2\pi\sqrt{LC}}$$

Where $f_r$ is the resonant frequency, L is the inductance, in Henries, of the inductor component, and C is the capacitance, in Farads, of the capacitor component. In this equation, there are three variables: $f_r$, L, and C. The resonant frequency, $f_r$, is a function of the MRI system of interest. As previously discussed, a 1.5T MRI system utilizes an RF system operating at approximately 64 MHz, a 3.0T system utilizes a 128 MHz RF, and so on. By determining the MRI system of interest, only L and C remain. By first selecting one of these two variable parameters, a filter designer needs only to solve for the remaining variable. Note, for a more accurate prediction of resonant frequency $f_r$, the PSPICE circuit of FIG. 23 should be used.

Figure 15:
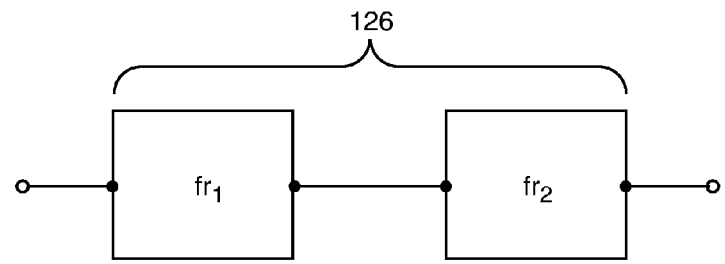
FIG. 15 is an electrical schematic diagram of the multilayer helical wave filter of FIGS. 13 and 14.

FIG. 15 is the schematic diagram of the multilayer helical wave filter of FIGS. 13 and 14 illustrating that the wave filter has multiple resonances at $fr_1$ and $fr_2$. For example, the multilayer helical wave filter 126 can be designed to be resonant at both 64 MHz (1.5-Tesla MRI) and 128 MHz (3-Tesla MRI). Accordingly, this would provide a very high impedance in the implanted lead during patient exposure to either one of these commonly available MRI scanners.

Figure 16:
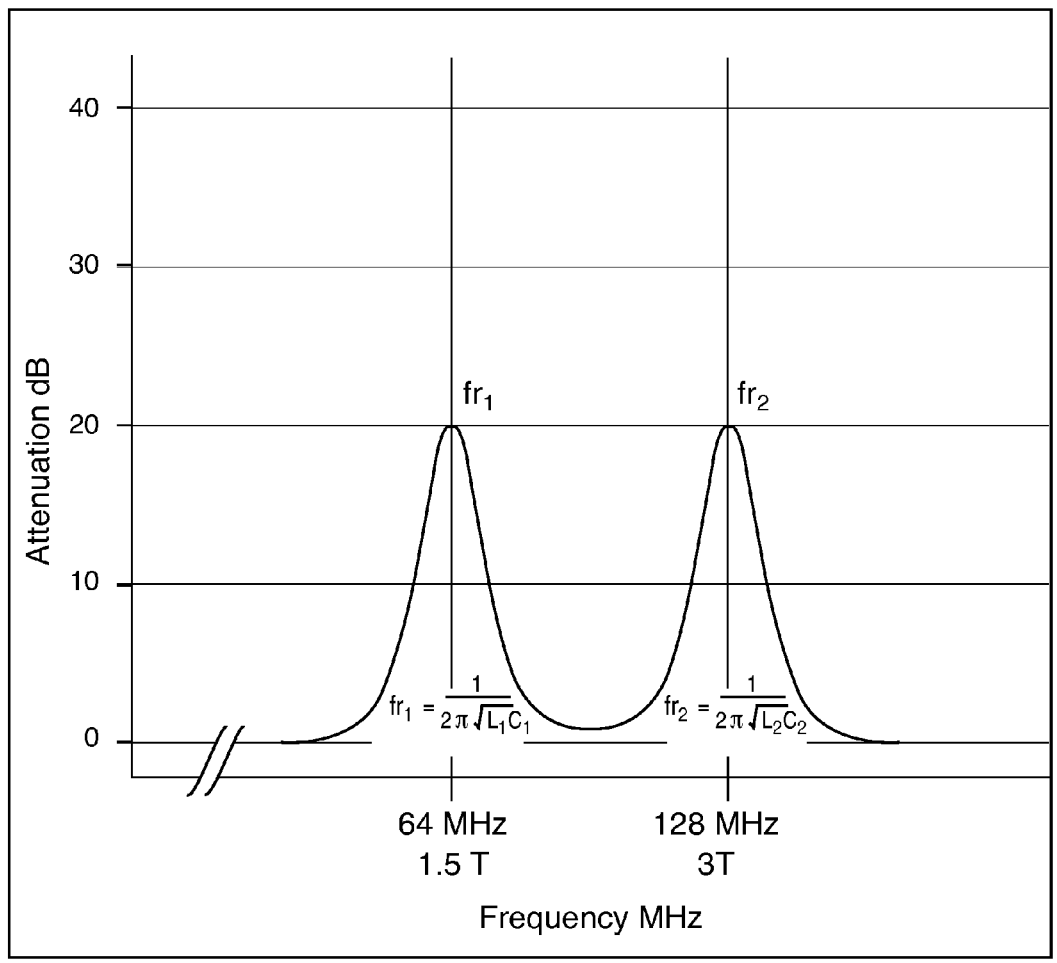
FIG. 16 is a graph of attenuation of the multilayer helical wave filter of FIGS. 13 and 14 versus frequency.

FIG. 16 is a graph of attenuation of the multilayer helical wave filter 126 of FIGS. 13 and 14 versus frequency in MHz. As one can see, there is a resonant peak at both $fr_1$ and $fr_2$ corresponding to 64 MHz and 128 MHz. In both cases, the impedance of the multilayer helical wave filter 126 is quite high which results in an attenuation value exceeding 10-dB. In general, the attenuation would be measured on a Spectrum Analyzer in a balanced 50-ohm system.

Figure 17:
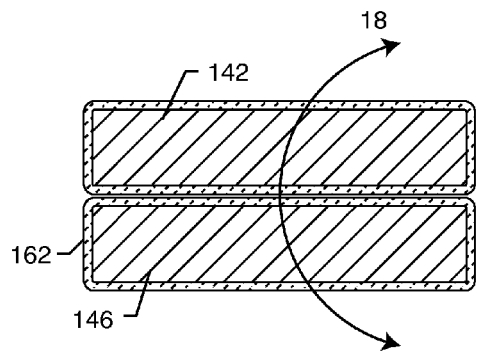
FIG. 17 is an enlarged sectional view taken of the area indicated by line 17-17 from FIG. 10.

FIG. 17 is taken generally along section 17-17 from FIG. 10. Shown is the end view of the elongated conductor that forms the first helically wound inductor segment 142 and the second helically wound inductor segment 146. One can see that in the preferred embodiment, the outer or first helically wound inductor segment 142 is wound very tightly to the second helically wound inductor segment 146. Preferably, there is little to no air gap in between. In addition, there is a dielectric or insulative coating 162 on the elongated conductor(s). This dielectric coating 162 is very important for two reasons: (1) it prevents adjacent turns from shorting and also prevents the first helically wound inductor segment 142 from shorting to the second helically wound inductor segment 146; and (2) the dielectric coating material has a much higher dielectric constant than air, thereby allowing one to increase or tune the capacitances 148 and 150.

Figure 18:
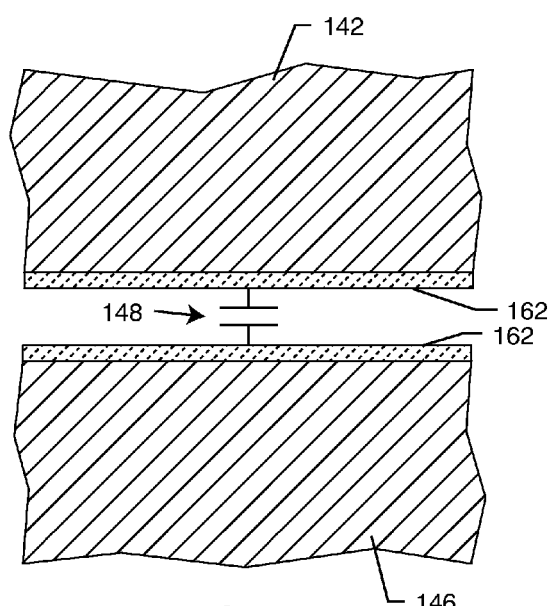
FIG. 18 is a sectional view taken generally along line 18-18 from FIG. 17, illustrating capacitance between adjacent helically wound segments.

FIG. 18 is taken generally along section 18-18 from FIG. 17. The capacitance 148 is shown. As previously described, the first helically wound inductor 142 would be wound tightly to the second helically wound inductor 146. However, in FIG. 18, they are shown separated for convenience so one can show the schematic symbol for the capacitor 148. The amount of parasitic capacitance 148 is determined by the overlap area of the outer helix segment and the inner helix segment. One can increase the amount of capacitance by increasing the width of the elongated conductors 142 and 146. The capacitance value is also related to the dielectric constant of the insulating material 162 and also the dielectric thickness of the insulting material 162. Reducing the dielectric thickness increases the capacitance value significantly. These relationships are expressed ideally by the following equation:

$$C = \frac{n \kappa A}{t},$$

where n is the number of overlapping capacitance areas, k is the dielectric constant of the insulating material, A is the effective capacitance area and t is the thickness between opposing plates. For the overlapping faces of the inner and outer segments of a multilayer helical wave filter, the effective capacitance area is relatively large since it includes the entire overlap area. This gives the designer many degrees of freedom in selecting the primary parasitic capacitance value 148.

Figure 19:
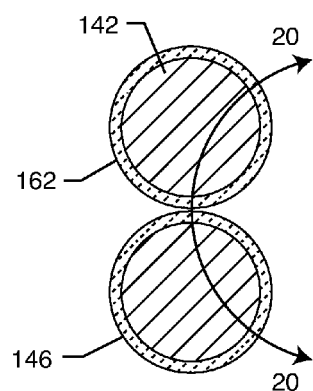
FIG. 19 is a view similar to FIG. 17, wherein the adjacent helically wound segments are round rather than rectangular.
Figure 20:
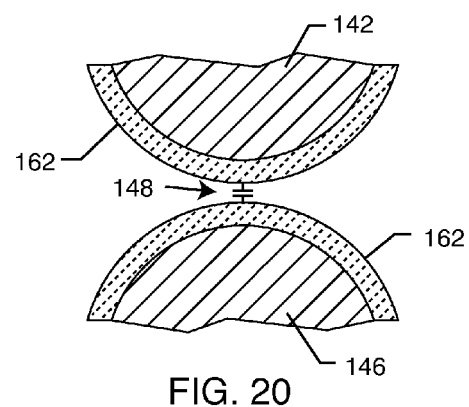
FIG. 20 is a sectional view taken generally along line 20-20 and similar to FIG. 18, illustrating capacitance between adjacent wires.

FIG. 19 is substantially the same as FIG. 17, except that the conductor is no longer rectangular or square in cross-section. The conductor shown in FIG. 19 would be a conventional round wire which would be highly undesirable in the present invention. As shown in FIG. 20, the effective capacitance (ECA) overlap area would be very small. Not only would the resulting capacitance be very small, but it would also be highly variable. As one can see, any slight variations in winding or winding alignment would cause the capacitance value of 148 to vary dramatically. Accordingly, it is a feature of the present invention that the elongated conductor 140 that forms the multilayer helical wave filter 126 be of either rectangular or square wire, preferably coated in a dielectric film 154 or the like. The size and shape of the elongated conductor that forms the helically wound segments is important. In general, a square or rectangular cross-section is preferred. By controlling the geometry and/or width of the elongated conductor that overlaps between the adjacent first helical segment and the second helical segment, one can control the parasitic capacitance that is formed. In other words, the designer can control the resonant frequency by controlling both the inductance and the amount of parasitic capacitance that is formed. Importantly, the designer can also control the Q and resulting 3-dB bandwidth at resonance of the multilayer helical wave filter. The primary factor in controlling the Q is to control the resistance of the wire that forms the first helical segment and the second helical segment. The resistivity of the wire is one of its primary material properties. One can choose from various materials to form the elongated conductor and the first and second helical segments. The resistance is also determined by the overall length of the elongated conductor of the first and second helical segments and also inversely related to its cross-sectional area (width times height). One also controls the parasitic capacitance by proper selection of the type of dielectric coating, the dielectric thickness and/or the distance between the inner and outer segments. This can be used to control second, third of even n resonant frequencies as well. A primary determining factor of the parasitic capacitance is the effective capacitance area which is determined by the amount of planar surface overlap between the first helically wound segment and the second helically wound segment. The first, second and third inductor segments can all be of the same cross-sectional shape and area elongated conductors and of the same number of turns. However, each segment could also have a different cross-sectional area of conductor and even a different number of turns. This affords the designer many degrees of freedom in controlling the inductance, resonant frequency and the Q of each resonant section.

There are several ways to apply the dielectric coating 154. One way would be to coat the entire elongated conductor wire 140 before forming the first and second helically wound inductor segments 142 and 146. Another way to do this would be through carefully controlled winding processes where the entire assembly was subsequently dipped or subjected to vacuum deposited dielectric material such as parylene. In another embodiment, a dielectric film could be disposed between the first helically wound inductor segment 142 and the second helically wound inductor segment 146. There are various suitable dielectric insulative materials such as Polyimide, aromatic polyimide, liquid crystal polymer, PTFE, PEEK, ETFE, Parylene, tantalum oxides, any nano-dielectric coating, PFA, FEP, Polyurethane, polyurethane with self-bonding overcoat, polyamide, polyvinyl acetal, polyvinyl acetal overcoated with polyamide, polyurethane overcoated with polyamide, epoxy, polyester (amide) (imide) overcoated with polyamide, polyester (amide) (imide), silicone-treated glass fiber, polyamide-imide, thermoplastic compounds, polyvinylchloride (PVC), polyolefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, crosslinked polyalkene, and various other types of polymer or ceramic materials. Different dielectric materials may be used for different sections of the multilayer helical wave filter. This would be to create different capacitance values and different resonance sections.

Figure 21:
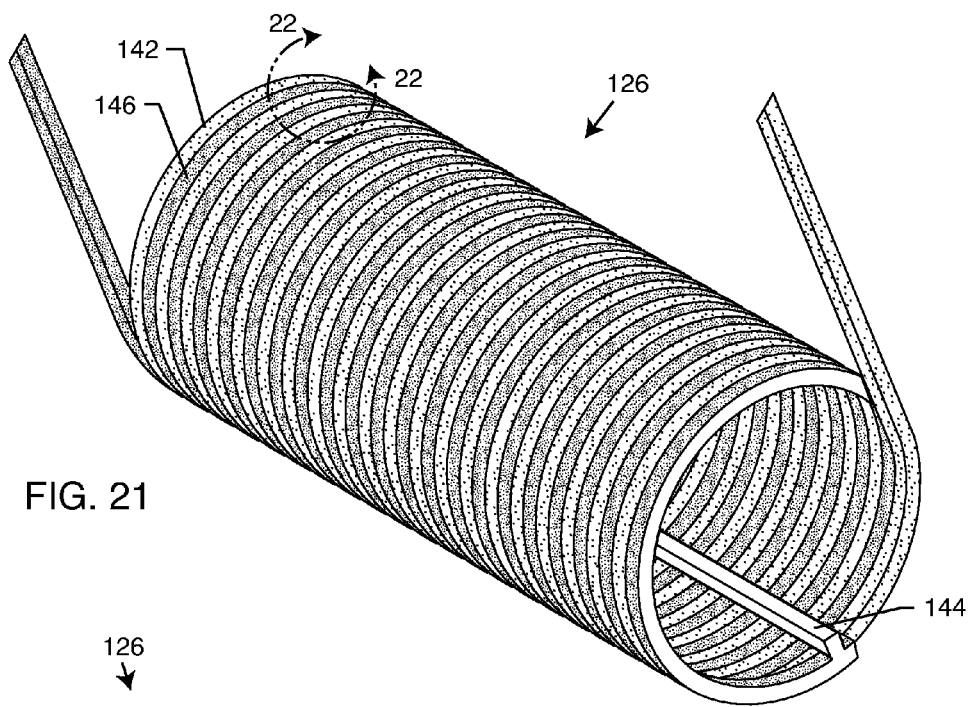
FIG. 21 is similar to FIG. 8, but illustrates an alternative embodiment wherein adjacent inductive segments are aligned side-by-side.

FIG. 21 illustrates an alternative construction of the multilayer helical wave filter 126 of the present invention. Referring back to FIGS. 8 and 9, one can see that the second helically wound inductor segment 146 is wound inside of the first helically wound inductor segment 142 on the same longitudinal axis. In FIG. 21, by way of contrast, one can see that the first helically wound inductor segment 142 and the second helically wound inductor segment 146 are wound adjacent to each other side-by-side along the same longitudinal axis. There is still a return wire 144 in order to make sure that the direction of turns of both the first helically wound inductor 142 and the second helically wound inductor 146 are in the same direction so that the RF currents are in the same direction as described in connection with FIGS. 8 and 9.

Figure 22:
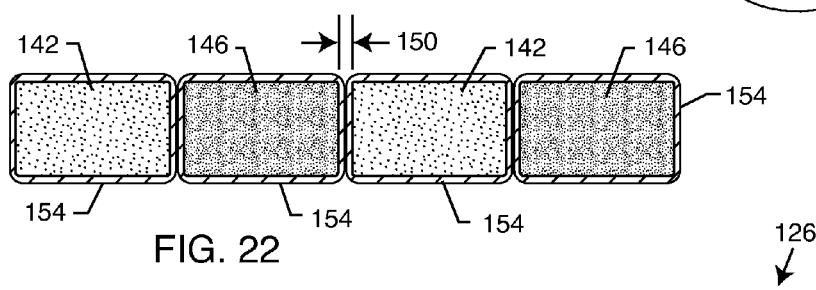
FIG. 22 is an enlarged sectional view taken generally along line 22-22 from FIG. 21.

FIG. 22 is taken generally along section 22-22 from FIG. 21. This shows the elongated conductor 140 of the first helically wound inductor segment 142 alongside the elongated conductor forming the second helically wound inductor segment 146. As can be seen, there is a capacitance 150 that is formed between the coils of the first helically wound inductor 142 and the second helically wound inductor 146 segments.

Figure 23:
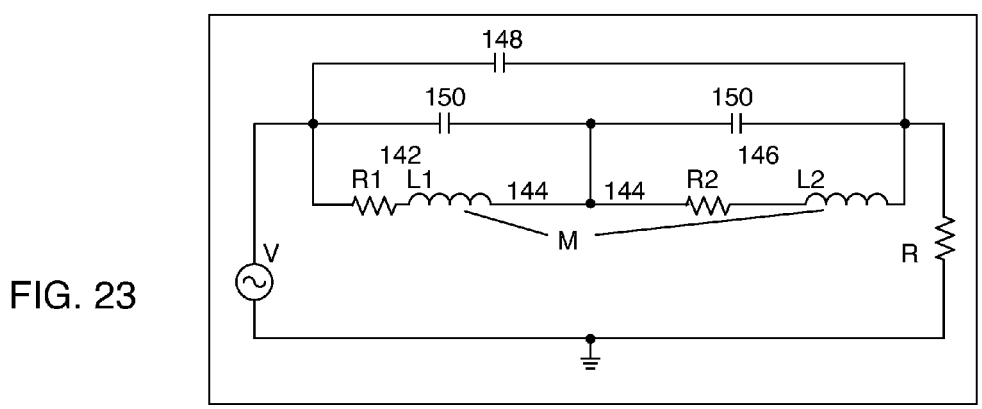
FIG. 23 is a simplified P-Spice electrical schematic diagram of the multilayer helical wave filter shown in FIGS. 8-10.

FIG. 23 is a simplified P-Spice schematic diagram of the multilayer helical wave filter 126 shown in FIGS. 8, 9 and 10. The voltage source shown in FIG. 18 would be the voltage induced in an implanted lead by a medical diagnostic procedure, such as by the RF field of an MRI scanner. The load resistance R is shown for simplification and would actually be a complex impedance based on the impedance of the lead system, body tissues and the input impedance of the active medical device (AMD). Those skilled in the art will understand that the capacitances and inductances and resistances of FIG. 23 would be distributed throughout the length of the multilayer helical wave filter 126. They are shown as lumped elements for simplicity. In FIG. 23, one can see the first helically wound inductor segment 142 consisting of L1 and resistance R1. The second helically wound inductor segment 146 is shown as inductance L2 and resistance R2. The resistance values R1 and R2 are determined by the classical resistance of any conductor wherein the resistance is proportional to the conductivity Rho (times) the length L (divided by) cross-sectional area A. The 3 dB bandwidth of the resonance of the multilayer helical wave filter 126 is determined by its Q at resonance. The Q is defined as the frequency of resonance (divided by) the change in (delta) 3 dB bandwidth $Q=f_r/\Delta f_{3\,dB}$. For a more complete description on this subject, one is referred to U.S. Pat. No. 7,363,090 and US 2011/0144734. As previously described, by controlling the inductance and capacitance of different sections, the multilayer helical wave filter 126 can be designed to have multiple resonances at different frequencies. Interestingly, one could also vary either the conductor 140 cross sectional area, material or length in different sections which would result in a different Q and 3-dB bandwidth at each resonant frequency. As one can see, the novel multilayer helical wave filter 126 affords the designer many opportunities to attenuate the current flow of one or multiple RF frequencies.

Figure 24:
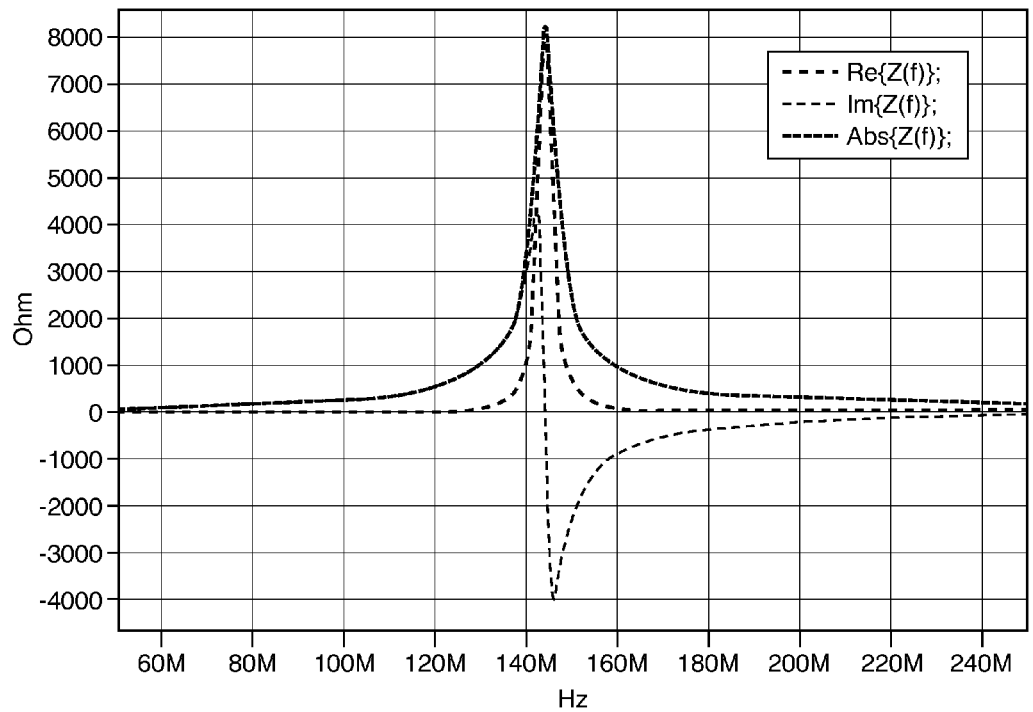
FIG. 24 is a graph illustrating the frequency response of a 20-turn coaxial two-layer helical bandstop filter of the present invention.

FIG. 24 is the frequency response of a 20 turn coaxial 2-layer helical wave filter 126 showing a resonant peak at 144 MHz. The cross-sectional area of the elongated conductor that forms the multilayer helical wave filter segments can vary in width anywhere from 0.0005 inches to 0.025 inches. The height of the rectangular square wire can also vary anywhere from 0.0005 inches to 0.025 inches. If the elongated conductor is round, the diameter can vary anywhere from 0.0010 to 0.025. The multilayer helical wave filter can be particularly designed for cardiac leads, wherein the diameter is typically anywhere from 2 French to 9 French (0.090 inches for 7 French or for neuro leads of 0.052 inches in diameter, which are typically 1 French. In general, the multilayer helical wave filter of the present invention can be built in any size from 1 French and above. Shown are the real part, the imaginary part and the absolute values of the impedance. One can also control the resistance R1 and R2 of the multilayer helical wave filter by proper conductor material selection. Biocompatible materials include MP35N, stainless steel and all of its alloys, tantalum, or drawn filled tubes. Drawn filled tubes can have a core of silver, gold, platinum or the like with an outer coating or tubing of MP35N, stainless steel 316LVN, nitinol or the like. Accordingly, one can control the inductance, the capacitance and the resistance of each segment of the multilayer helical wave filter individually. The resistance will largely determine the Q and the 3-dB bandwidth at each resonance point.

Figure 25:
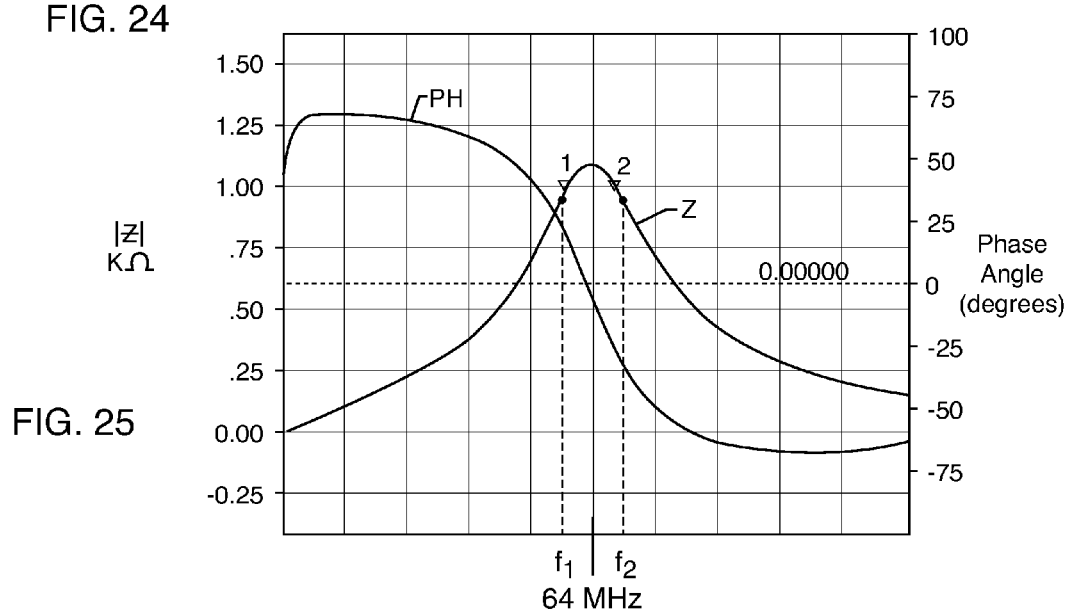
FIG. 25 is a graph showing the frequency response for the multilayer helical wave filter of FIGS. 8-10, which has been modified to show resonance through a frequency range corresponding to the RF pulsed frequency for a 1.5 Tesla MRI scanner.

FIG. 25 shows the helical wave filter 126 of FIG. 8 and FIG. 9 has been modified to show the inductance and the capacitance values 148 and 150 such that the multilayer helical wave filter is resonant at 64 MHz, which corresponds to the RF pulsed frequency for 1.5 Tesla MRI scanners. As can be seen on the left vertical axis, the impedance Z is plotted in kilohms. On the right vertical axis, the phase angle is plotted in degrees. One can see that there is a phase shift from positive to negative that corresponds with the resonant center frequency of 64 MHz. Markers 1 and 2 shown on the impedance curve correspond with frequencies $f_1$ and $f_2$. These are the 3-dB down points. The 3-dB bandwidth is preferably 10 kHz or greater and is the difference in frequency of $f_2-f_1$. The 3-dB bandwidth would be best measured in a Spectrum or Network analyzer in a balanced 50 ohm system measuring attenuation. One can see that the multilayer helical wave filter 126 of the present invention provides over 1000 ohms (1 kilohm) of impedance at the MRI RF pulsed frequency. This provides a dramatic amount of attenuation and current reduction thereby preventing implanted leads and/or their associated electrodes from overheating during an MR scan. Optimal selection of materials and dielectrics can provide up to 5 to 10 kilohms of impedance at resonance. As previously mentioned, in order to provide this high impedance at resonance, it is critical that the multilayer helically bandstop filter be insulated such that RF currents cannot conduct around it through body fluids or tissues thereby degrading the impedance through these parallel paths.

Figure 26:
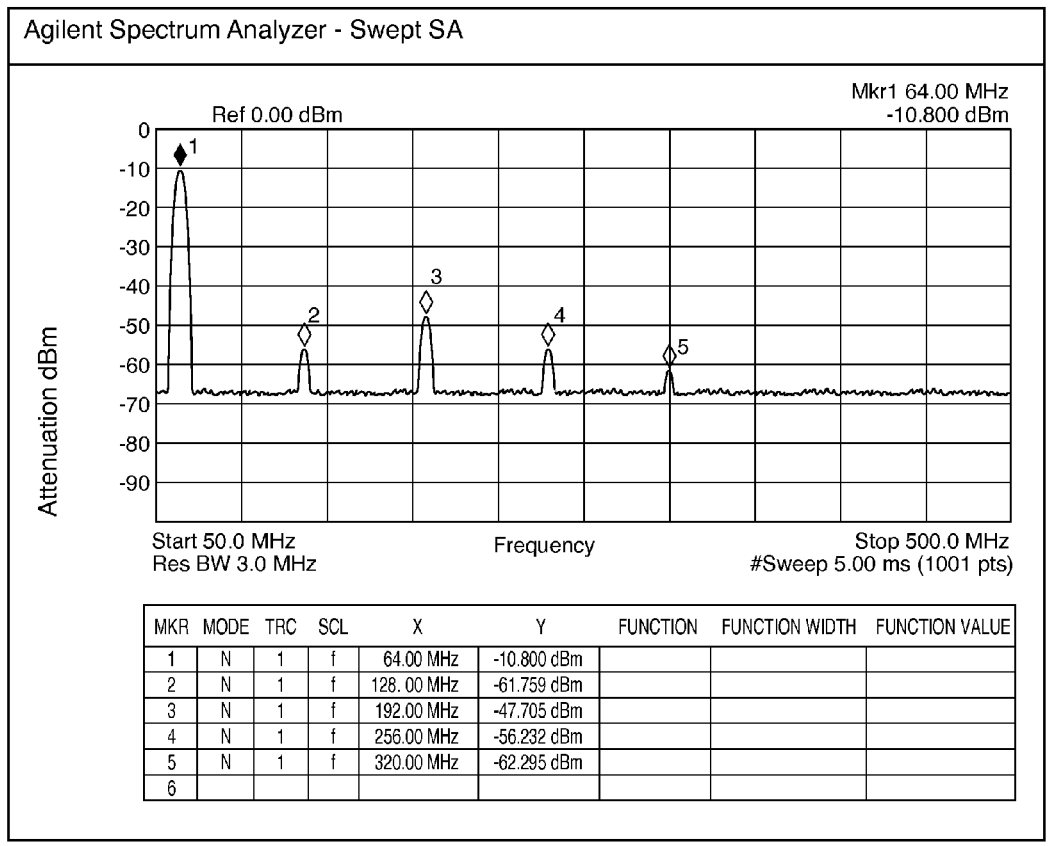
FIG. 26 is a Spectrum Analyzer scan taken from an RF probe located inside a 1.5 Tesla clinical MRI scanner.

FIG. 26 is a Spectrum Analyzer scan taken from an RF probe located inside a 1.5 Tesla clinical MRI scanner. The primary RF pulsed frequency is shown as marker 1 as 64 MHz. The harmonics of the RF pulsed frequency are generally not specified or controlled by manufacturer specifications or industry standards. In other words, these harmonics are largely uncontrolled. The scan shows a harmonic (marker 2) at 128 MHz, a harmonic (marker 3) at 192 MHz, a harmonic (marker 4) at 256 MHz and even a harmonic at 320 MHz (marker 5). The primary RF pulsed frequency (64 MHz) and its harmonics can all contribute to RF currents in a lead and particularly RF currents at a distal electrode to tissue interface. Accordingly, the primary frequency and its harmonics can all contribute to leadwire heating.

The multilayer helical wave filter can be designed to have resonances at the primary MRI RF frequency (64 MHz) and also at some or all of its harmonic frequencies. In general, only harmonics of significant amplitude would require attenuation by the multilayer helical wave filter.

Figure 27:
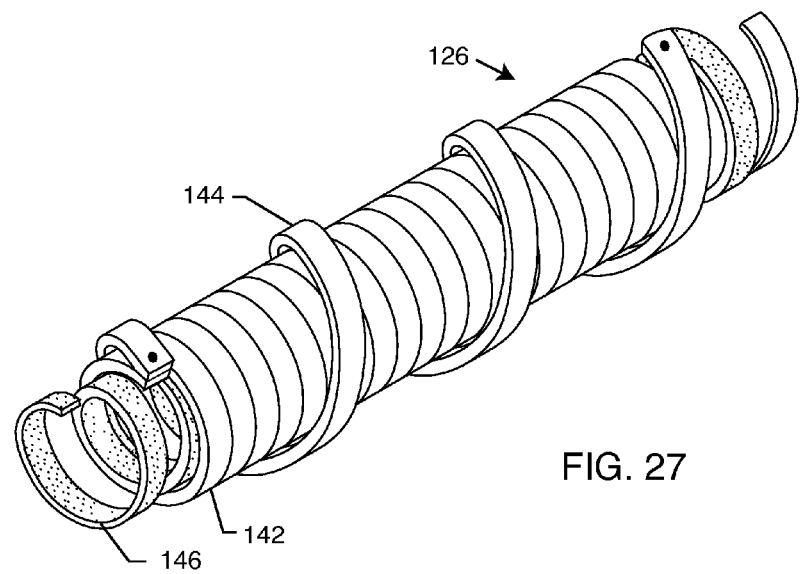
FIG. 27 is an isometric view similar to FIG. 8, except that the connecting segment has been curled around the outside of both the first and second helically wound inductor segments.

FIG. 27 is similar to FIG. 8 except that the connecting segment 144 has been coiled around the outside of both the first helically wound inductor 142 and second helically wound inductor 146 segments. Coiling of the return wire 144 decreases its inductance and increases its capacitance. By changing the inductance of the return wire 144, one controls the phase shift between the RF currents in various segments as previously described. This can be used to introduce a secondary resonance into the multilayer helical wave filter 126 in such a way to provide attenuation at multiple MRI RF pulsed frequencies. For example, attenuation could be provided at both 64 MHz (1.5 Tesla) and 128 MHz (3 Tesla). It will be obvious to one skilled in the art that the multilayer helical wave filter can be designed to have one, two, three or . . . n-resonant frequencies.

Figure 28:
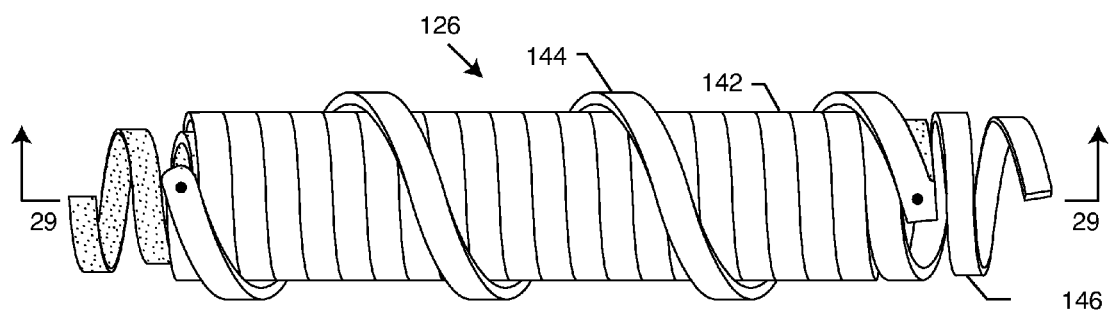
FIG. 28 is side view of the structure shown in FIG. 27.

FIG. 28 is the side view of the multilayer helical wave filter 126 shown in FIG. 27.

Figure 29:
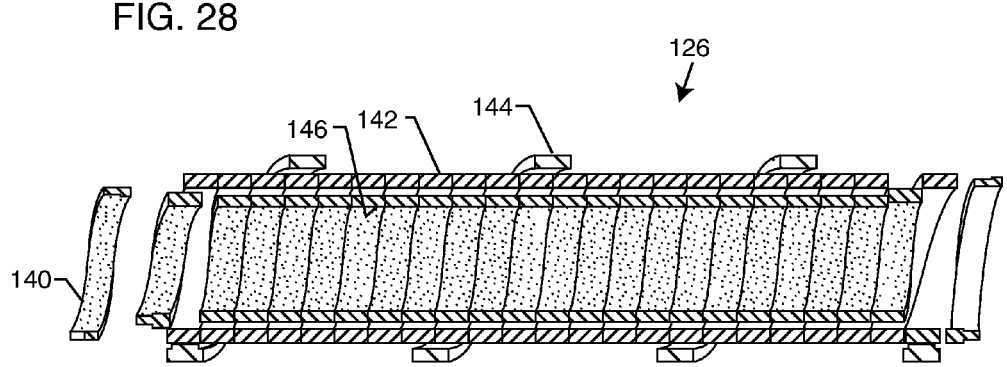
FIG. 29 is a sectional view taken generally along line 29-29 from FIG. 28.

FIG. 29 is a sectional view taken generally along line 29-29 from FIG. 28. Shown is the elongated conductor 140 of the first helical wound segment 142, the second helically wound segment 146 and the connecting segment 144. A coiled return wire 144 could be applied to any of the previously described multilayer helical wave filters 126 such as shown in FIG. 8, 9, 13 or 21.

Figure 30:
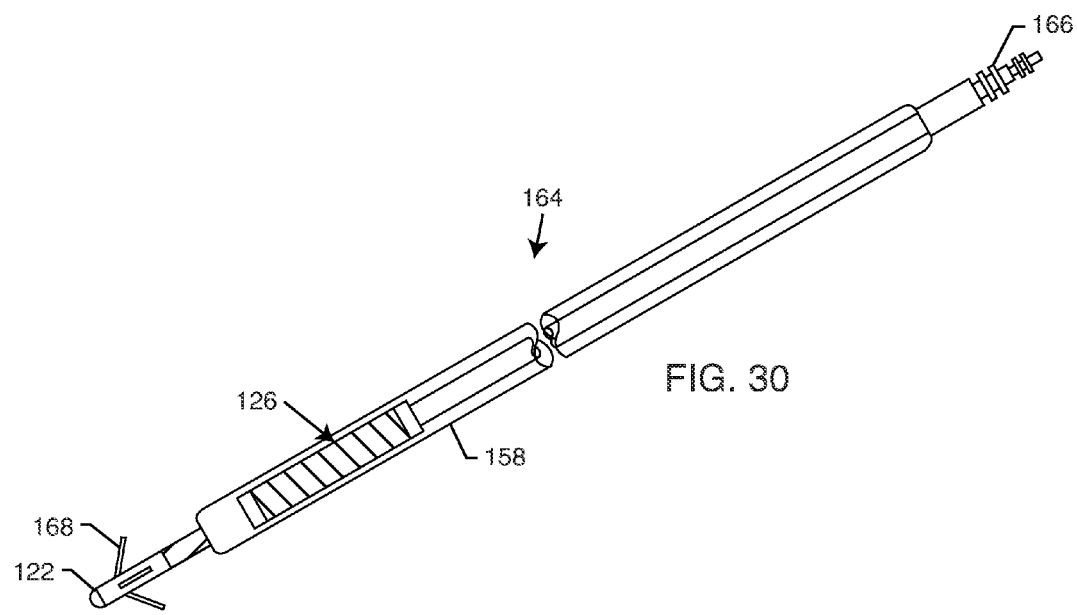
FIG. 30 is an elevational view of a unipolar pacemaker lead having a proximal connector with an embedded multilayer helical wave filter in accordance with the present invention.

FIG. 30 illustrates a unipolar pacemaker lead 164 having a proximal connector 166 such as described by International Standards ISO-IS1, DF1, DF4 or IS4. This proximal connector 166 would be plugged into a cardiac pacemaker, a cardioverter defibrillator or the like (not shown). The distal end of the lead has a tip electrode 122 with tines 168 which are used to grasp trabecular or other tissue within a human heart. Shown is a multilayer helical wave filter 126 of the present invention that is located near or at the distal unipolar electrode 122. Referring once again to FIG. 30, one can see that the lead body has an overall insulation 158 which extends over the multilayer helical wave filter to a point near the distal electrode 122. This insulation is critically important to prevent RF currents from circulating through the body fluids thereby tending to short out or degrade the impedance of the multilayer helical wave filter 126. In a preferred embodiment, the overall insulation 158 still provides that the center of the multilayer helical wave filter can be hollow for convenient guide wire insertion. In addition, the center of the wave filter could incorporate one or more valves such that additional leads or guide wires placed from the proximal side can be routed and sealed. Access from the distal side would be restricted in a similar manner to a hemostasis valve in an introducer. As previously described, when exposed to an MRI high intensity RF environment, the multilayer helical wave filter 126 impedes the undesirable flow of RF currents into body tissues via electrode 122. Referring once again to FIG. 30, one can see that the lead body has an overall insulation 158 which extends over the multilayer helical wave filter to a point near the distal electrode 122. This insulation is critically important to prevent RF currents from circulating through body fluids thereby tending to short out or degrade the impedance of the multilayer helical wave filter 126. Thereby the multilayer helical wave filter 126 prevents overheating of the distal electrode 122 and/or the surrounding body tissues. It has been shown, that overheating of said tissues can cause changes in pacemaker capture threshold or even complete loss of pacing.

Figure 31:
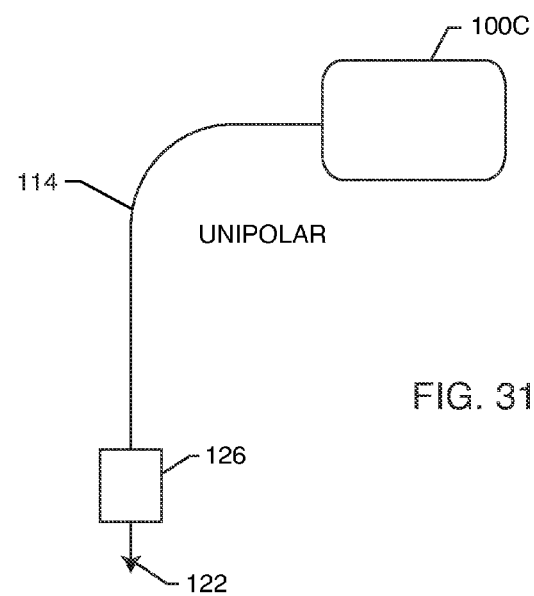
FIG. 31 is a schematic diagram of the unipolar lead of FIG. 30.

FIG. 31 is a schematic diagram of the unipolar lead 164 of FIG. 30 showing the AMD 100C and a multilayer helical wave filter 126 of the present invention installed preferably at or near the distal tip electrode 122.

Figure 32:
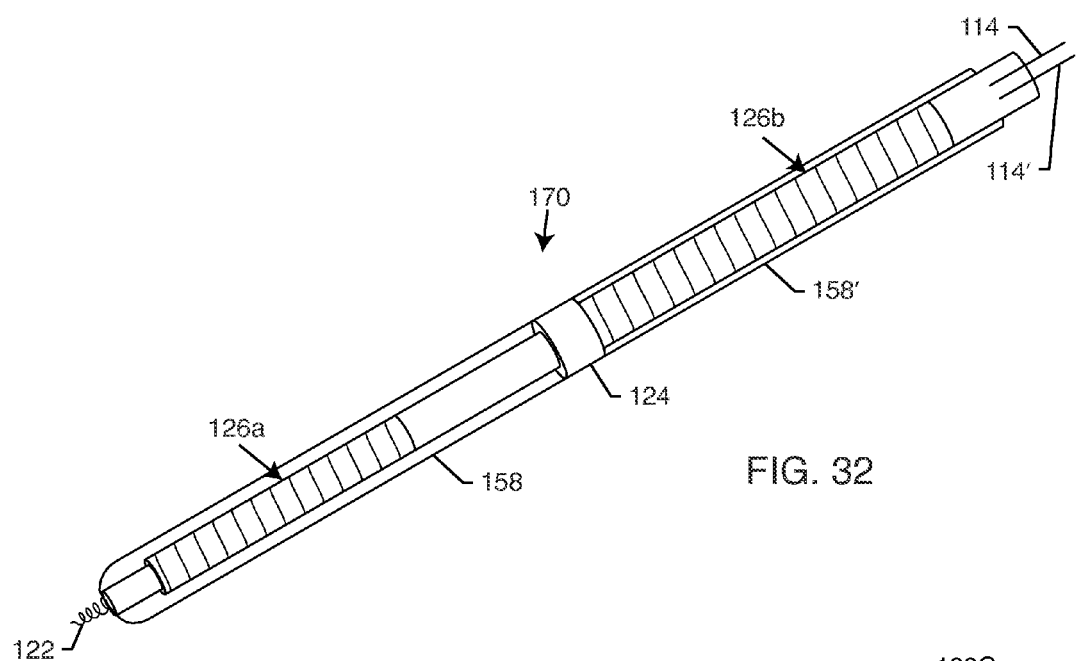
FIG. 32 is a view similar to FIG. 30, except that the multilayer helical wave filter of the present invention is associated with the tip and ring electrodes of an active fixation tip.

FIG. 32 is very similar to FIG. 30 except a bi-polar active fixation electrode 170 is shown at the distal end or tip of the implanted lead. In this case, the screw-in helix tip electrode 122 has been extended, which would typically be screwed into cardiac tissue. A ring electrode 124 forms a bi-polar electrode system wherein pacing and sensing can be conducted between the helix tip electrode 122 and the ring electrode 124. There would be two conductors 114 and 114' in this case that would be routed to and plugged into the active medical device. There is a multilayer helical wave filter 126a in series with the helix electrode 122 and also a multilayer helical electrode 126b in series with the ring electrode 124. In this way, both the distal helix 122 and ring electrodes 124 would both be prevented from overheating in an MRI environment. Insulation 158 prevents RF currents from flowing through body fluids and shorting out multilayer helical wave filter 126a and insulation material 158' insulates multilayer helical wave filter 126b and performs the same function. In addition, the insulating layer 158 also protects the implanted lead, provides flexibility and lubricity and aids in the long-term reliability of the overall lead system.

Figure 33:
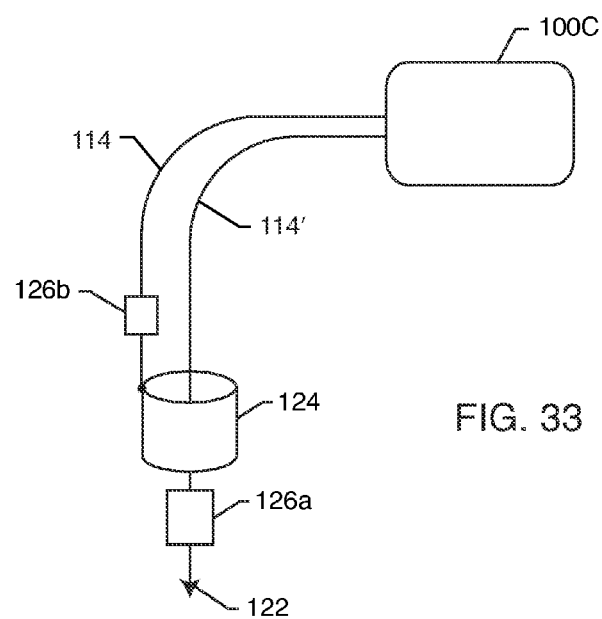
FIG. 33 is an electrical schematic diagram of the bi-polar active fixation electrode illustrated in FIG. 32.

FIG. 33 is the schematic diagram of the bi-polar lead previously illustrated in FIG. 32. One can see the active implantable medical device such as a cardiac pacemaker 100C with implanted lead conductors 114 and 114'. Lead conductor 114 is directed in series with a multilayer helical wave filter of the present invention to ring electrode 124. Lead conductor 114' has multilayer helical wave filter 126a in series with tip electrode 122. As previously described, in preferred embodiments, the multilayer helical wave filter 126a and 126b are very near or at the respective distal electrodes. This prevents RF current induction from MRI fields from coupling around the wave filters and inducing currents in the distal electrodes.

Figure 34:
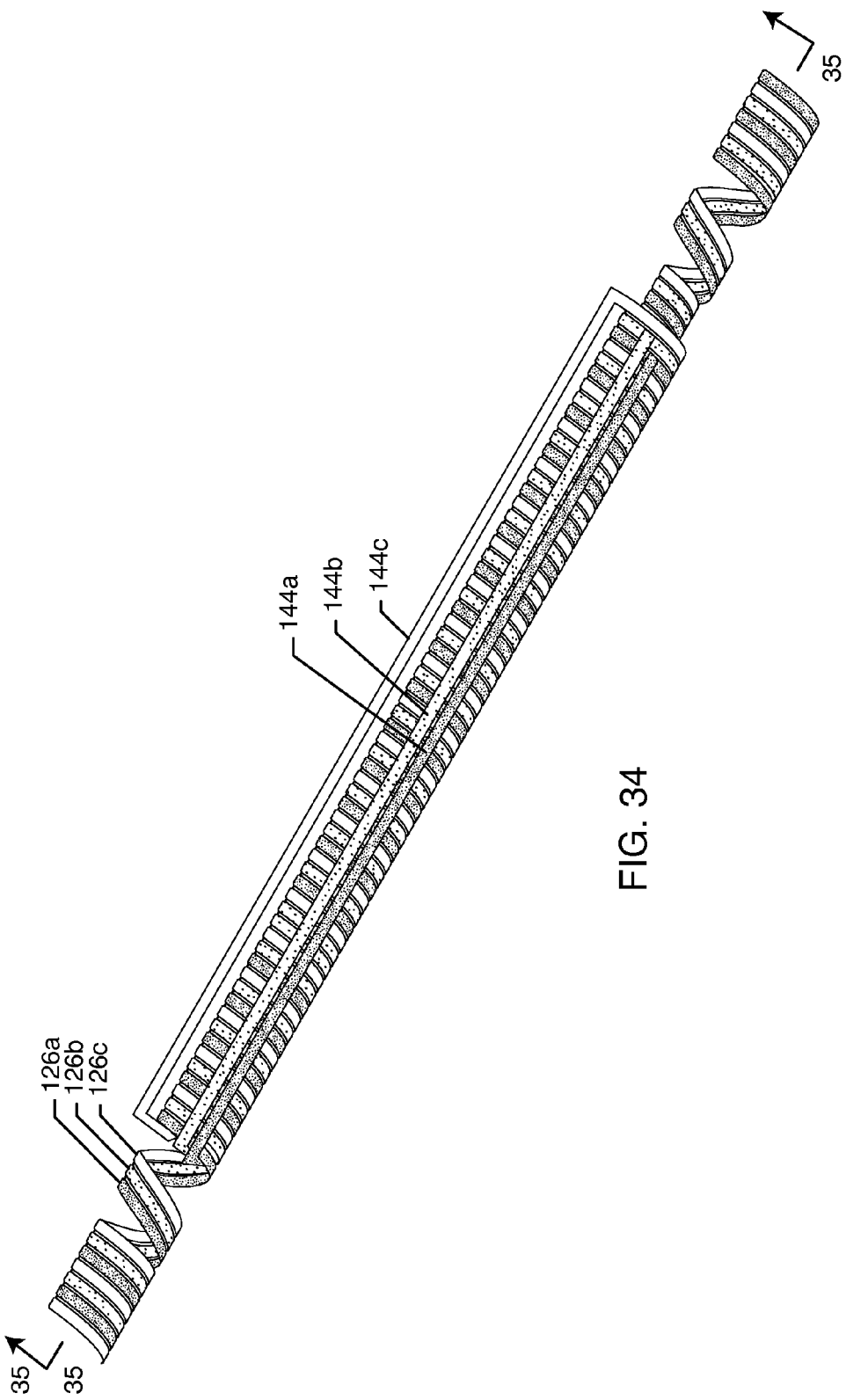
FIG. 34 is an elevational view of the formation of three multilayer helical wave filters wound about a common longitudinal axis.

FIG. 34 illustrates the formation of three multilayer helical wave filters 126a, 126b and 126c of the present invention. As shown in FIG. 36, these could be split out to be placed in series with three different electrodes 122a, 122b and 122c. This arrangement is particularly advantageous for neuro-stimulator applications where there might be 3, 6, 12, 16, 24 or even "n" electrodes. Accordingly, multilayer helical wave filters 126 can be wound to be in series with any number of such electrodes (n-electrodes). Any number (m) of these "n" multilayer helical wave filters can also be used in a neuro lead wherein the number of electrodes becomes =n=m. In other words, a neuro electrode matrix can be easily formed by the multilayer helical wave filter of the present invention.

FIG. 35 is a sectional view of the three electrode configurations illustrated in FIG. 34. The filter region consists of three multilayer helical wave filters of the present invention. That, in turn, is connected to the implanted lead. Electrodes 122a, 122b and 122c are typically the ring or pad electrodes of a neural lead.

FIG. 36 is the schematic diagram of the three electrode multilayer helical wave filter of FIG. 35. Shown are three multilayer helical wave filter segments 126a, 126b and 126c shown in series with each of the three ring or paddles electrodes 122a, 122b and 122c. Each of the conductors of the implanted lead 114a, 114b and 114c are shown connected to the active implantable medical device 100C.

Figure 37:
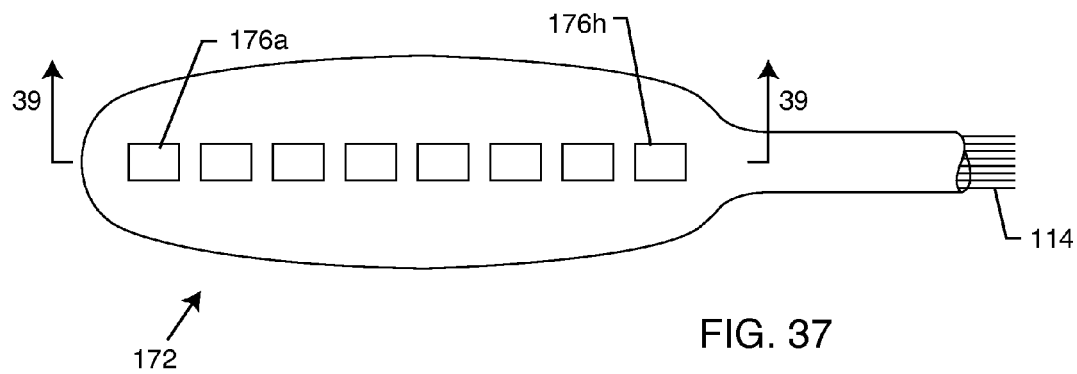
FIG. 37 is an elevational view of an 8-pin paddle electrode.

FIG. 37 illustrates an 8-pin paddle electrode 172 commonly used in spinal cord stimulator applications. The eight paddle electrodes are shown as 176a through 176h.

Figure 38:
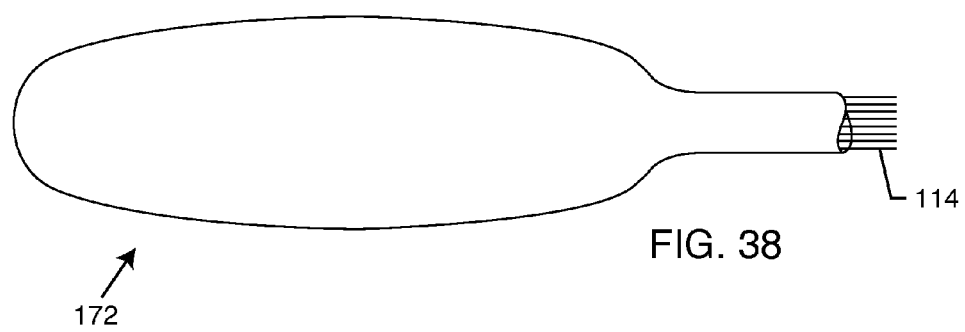
FIG. 38 is an elevational view of the reverse side of the paddle electrode shown in FIG. 37.

FIG. 38 is the reverse side of the paddle electrode 172 of FIG. 37.

Figure 39:
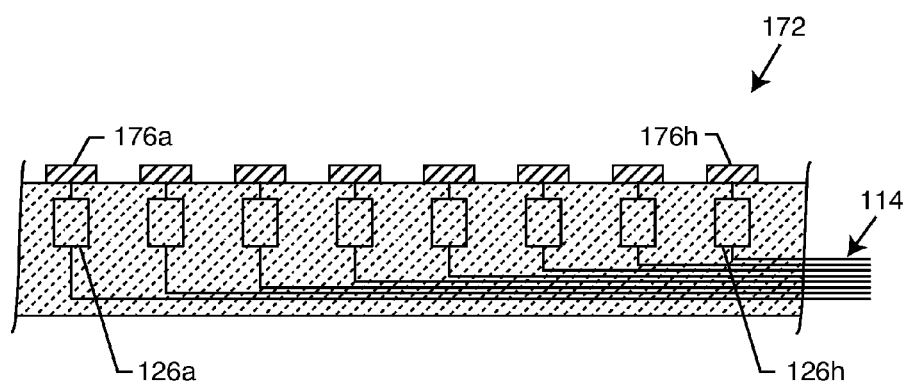
FIG. 39 is an enlarged sectional view taken generally of the area indicated by line 39-39 from FIG. 37.

FIG. 39 is a cross-section taken generally from section 39-39 from FIG. 37. One can see that there is a multilayer helical wave filter 126 in series with each one of the pad electrodes 176. FIG. 39 is just a representative example. As used herein, electrodes shall include any type of electrode in contact with body tissue. This includes, but is not limited to, pacemaker electrodes, endocardial electrodes, epicardial electrodes, defibrillator shocking coils, tip electrodes, ring electrodes, ablation electrodes, deep brain electrodes, nerve cuff electrodes, various types of paddle electrodes, cochlear electrode bundles, Bions, probe and catheter electrodes and the like.

Figure 40:
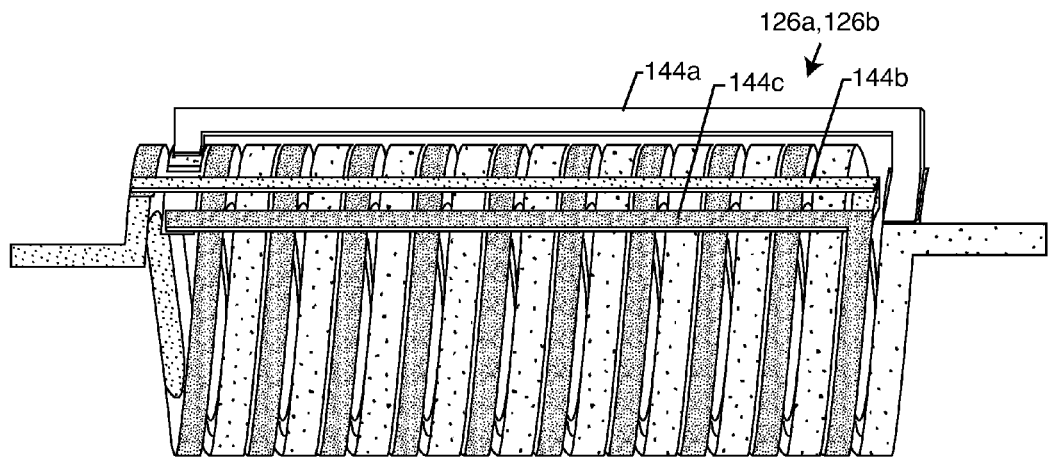
FIG. 40 is an elevational view of another embodiment for a multilayer helical wave filter embodying the present invention, wherein three return conductors are provided to perform two discrete multilayer helical wave filters that are in series with each other.

FIG. 40 is a special multilayer helical wave filter with three return conductors 144a, 144b and 144c which form two discrete multilayer helical wave filters 126a and 126b that are in series with each other. In accordance with the present invention, each one would have a selected RF resonant frequency. In a preferred embodiment, the first resonant frequency $f_{r1}$ would be the RF pulsed frequency of a 1.5-Tesla common MRI scanner at 64 MHz. The second multilayer helical wave filter portion would be resonant $f_{rz}$ at 128 MHz which is the RF pulsed frequency for commonly available 3-Tesla MR scanners. By varying the cross-sectional area of the elongated conductor and also the pitch and number of turns, in addition to the dielectric material and separation between the inner and outer coils, the resonant frequencies $f_{r1}$ and $f_{r2}$ can be precisely tuned.

Figure 41:
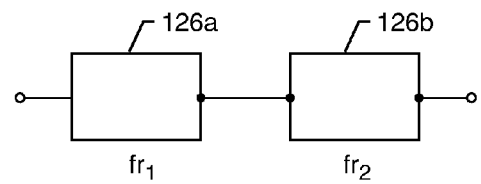
FIG. 41 is a schematic diagram of the multilayer helical wave filter of FIG. 40.

FIG. 41 is a schematic diagram of the multilayer helical wave filter of FIG. 40 showing that it provides (in one package) for two resonances in series which are shown as $f_{r1}$ and $f_{r2}$.

Figure 42:
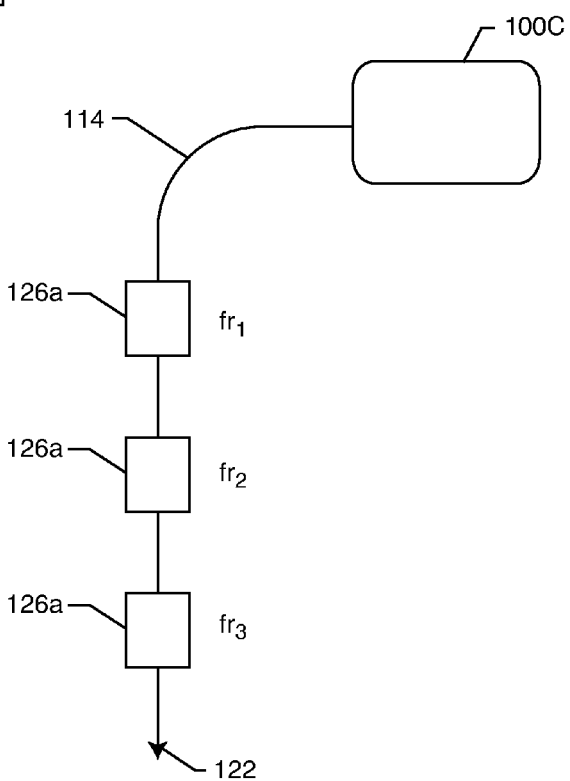
FIG. 42 is a schematic illustration showing that any number of individual multilayer helical wave filters can be placed in series in any conductor of any implanted lead.

FIG. 42 illustrates that any number of individual or separate discrete multilayer helical wave filters 126 can be placed in series in any conductor of any implanted lead in multiple locations along the lead length. For example, referring once again to FIG. 8, three different helical wave filters could be placed in series along the length of an implanted lead as shown. In FIG. 42, there are three different helical wave filters that are resonant at $f_{r1}$, $f_{r2}$ and $f_{r3}$. It will be obvious to those skilled in the art that any number of helical wave filters can be placed in series in an implanted lead. In summary, multiple resonances $fr_1$ and $fr_2$ . . . or $fr_n$ can be created by multiple segments in a single multilayer helical wave filter or multiple resonances can also be achieved by installing a multiplicity of discrete wave filters along the length of the lead as shown in FIG. 42.

Figure 43:
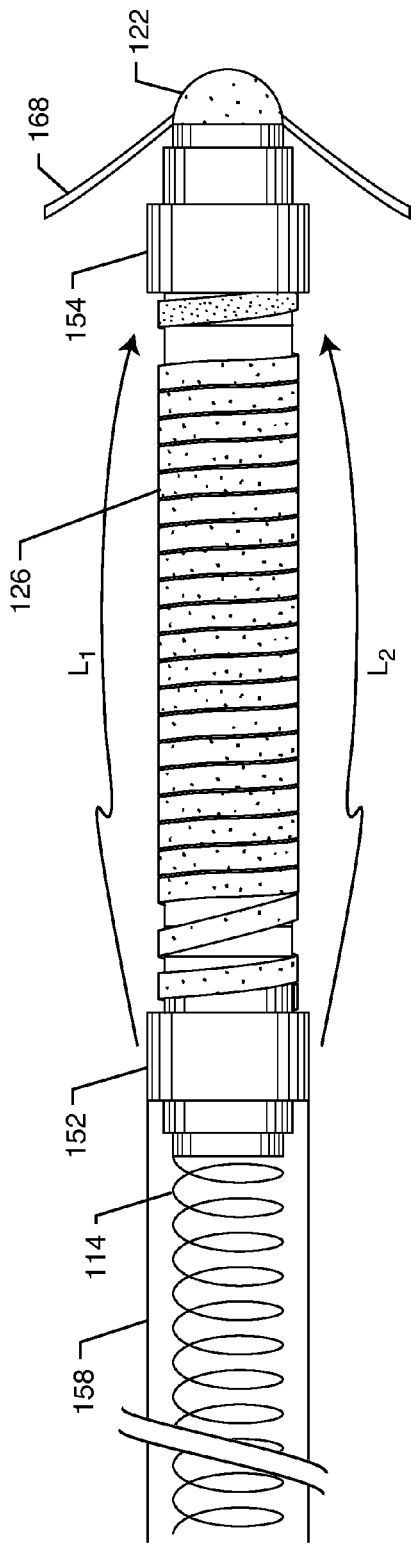
FIG. 43 is an elevational view of the multilayer helical wave filter of FIG. 11 shown in series with a passive fixation electrode and an implanted lead.

FIG. 43 illustrates the multilayer helical wave filter 126 with end caps 152 and 154 that were previously illustrated in FIG. 11. End cap 152 is shown attached to the conductor 114 of an implanted lead 158 which has an overall insulation sheath 158. In this case, by way of example, the multilayer helical wave filter 126 presents 2000 ohms at its primary resonant frequency of 64 MHz. However, in this configuration, since the multilayer helical wave filter is not have overall end to end insulation, there are undesirable RF leakage pads $L_1$ and $L_2$ through body tissue. The 2000 ohms of impedance desirably impedes the flow of MRI induced RF currents into body tissue through the electrode 122. However, if both ends of the multilayer helical wave filter are not isolated from each other, parallel paths result through body fluid (ionic fluid). This parallel path as measured by the inventors can be approximately 80 ohms. Referring back to FIG. 43, if an 80 ohms parallel path existed between the end caps 152 and 154, this would seriously degrade the impedance at resonance. The amount of degradation in impedance can result in RF currents flowing through the distal electrode 122 into body tissues that could result in life-threatening overheating of these adjacent tissues.

Figure 44:
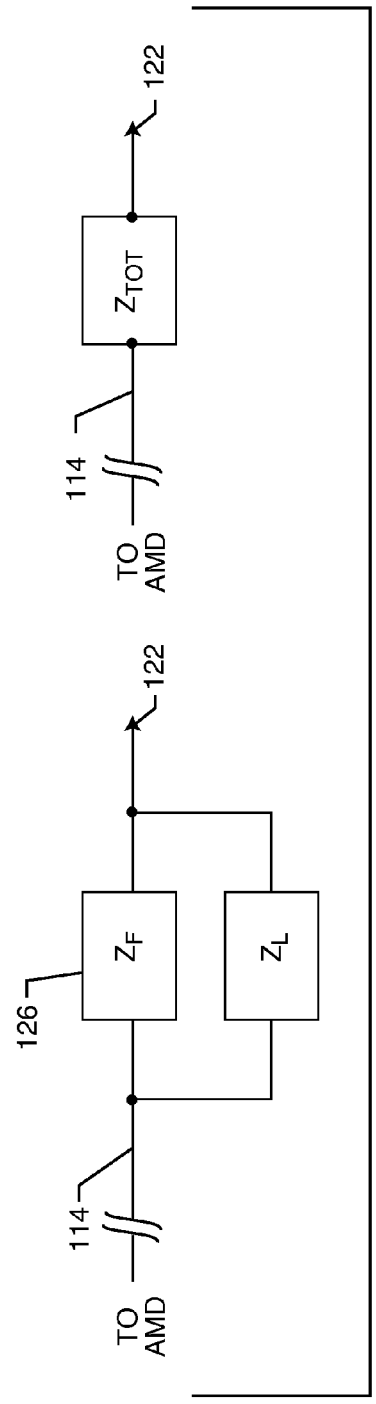
FIG. 44 is a schematic diagram which illustrates undesirable electrical leakage through body fluids in parallel with the multilayer helical wave filter of FIG. 43.

FIG. 44 is the schematic diagram taken from FIG. 43 showing the 2000-ohm impedance $Z_F$ of the multilayer helical wave filter 126. Shown in parallel with the multilayer helical wave filter 126 is the leakage path or 80-ohm impedance of the body tissues $Z_L$. Using the parallel resistance formula, when one has 80 ohms in parallel with 2000 ohms, the result is a combined impedance $Z_{TOT}$ of 76.82 ohms. As one can see, this is a catastrophic reduction of the impedance of the multilayer helical wave filter at resonance. It is a critical feature of the present invention that these body fluid paths be insulated so that they cannot cause leakage in parallel with the multilayer helical wave filter of the present invention.

Figure 45:
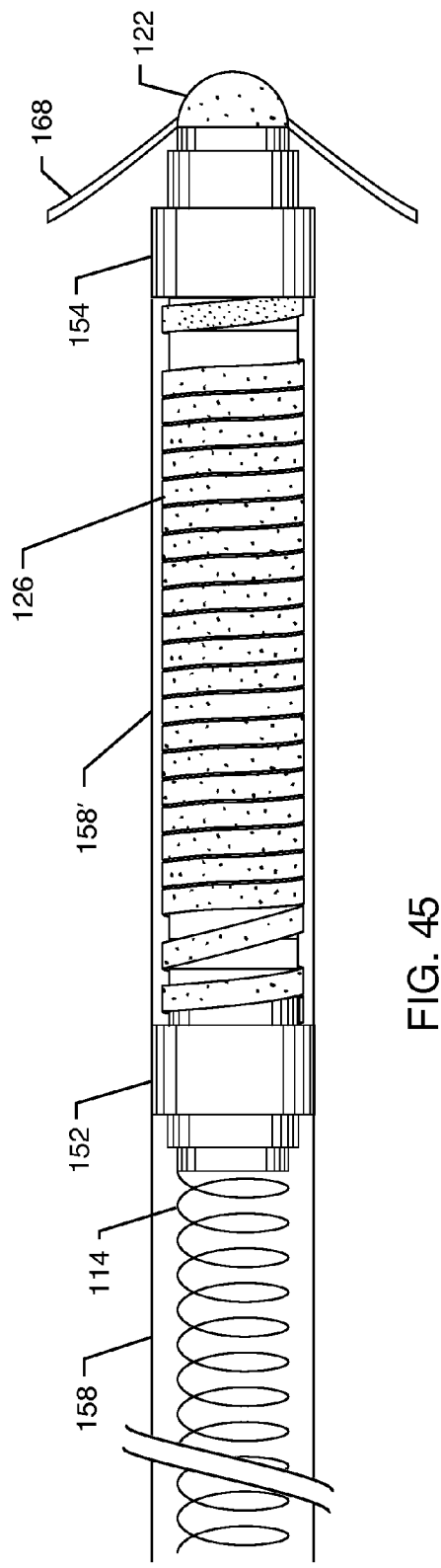
FIG. 45 is an elevational view of the multilayer helical wave filter of FIG. 43 with electrical insulation disposed over the multilayer helical wave filter such that electrical leakage through body fluids is prevented.

FIG. 45 is very similar to FIG. 43 except that the lead insulation 158' has been extended completely over the multilayer helical wave filter 126 of the present invention. Accordingly, the leakage paths through ionic body fluid $L_1$ and $L_2$ have been eliminated. In this case, the multilayer helical wave filter of FIG. 45 would present the full 2000 ohms of impedance at the MRI RF-pulsed frequency.

Figure 46:
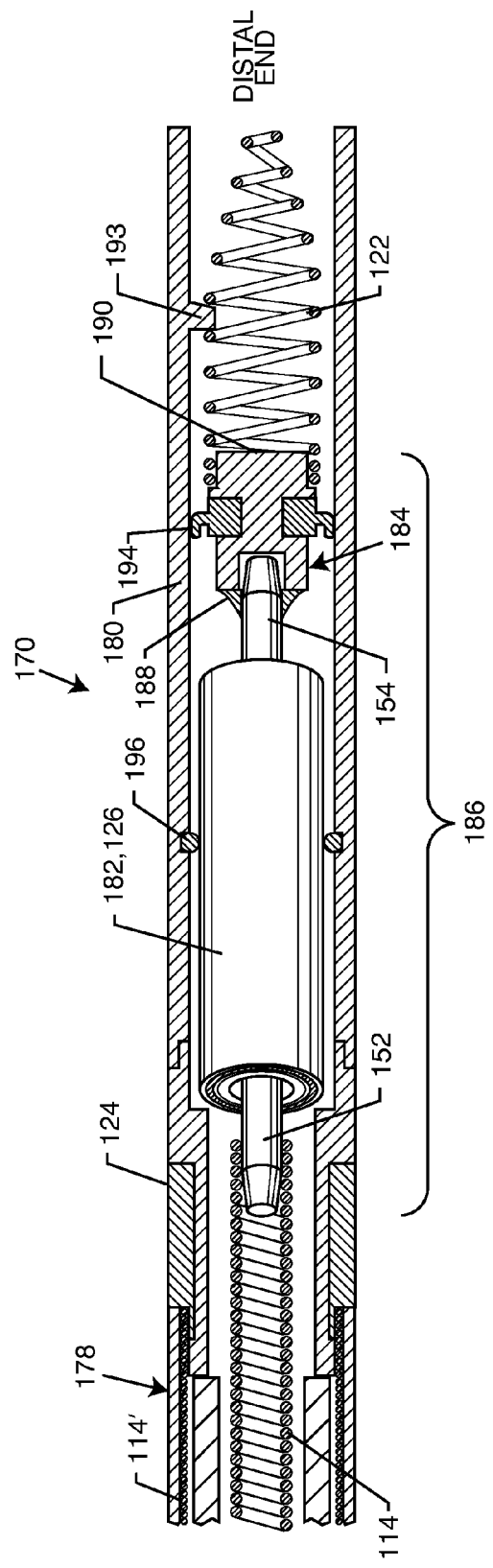
FIG. 46 is a sectional view of an active fixation electrode assembly embodying a multilayer helical wave filter with seals to prevent ingress of body fluids.

FIG. 46 illustrates an active fixation helix tip electrode assembly typically used in cardiac pacemaker applications. Shown is a multilayer helical wave filter 126 of the present invention. In this case, the multilayer helical wave filter is shown in a hermetic subassembly 180. Electrically isolating electric components in a medical electric lead with an active fixation electrode are described in US 2010/0324240 (see FIG. 10) the contents of which are incorporated herein.

FIG. 46 illustrates an exemplary bipolar active fixation electrode 170 which embodies a lead body 178, a coaxial conductor 114' for the ring electrode 124 and coaxial conductor 114 for the tip (active fixation helix) electrode 122, a collar 180, and the translatable casing 182 which houses a multilayer helical wave filter 126 of the present invention. The translatable casing 182 includes a pins 152 and 154. The pin 152 is electrically and mechanically connected to the tip electrode lead wire conductor 114 and the pin 154 is attached to the translatable seal assembly 184 which is also connected to a distal helix electrode 122. The distal helix electrode 122 is also known as an active fixation electrode. The pin 152, the casing 182, the pin 154 and the translatable seal structure 184 all form what is defined herein as a casing subassembly 186. A casing 182 which houses the multilayer helical wave filter 126 can be a hermetic seal as previously described in FIG. 10 or US 2010/0324640 or it can be a rigid or semi-rigid subassembly similar to that previously illustrated in FIG. 11 herein. As previously described, it is very important that body fluids be prevented from encroaching across the two ends 152 and 154 of casing 182 and the multilayer helical wave filter 126. As previously described, these parallel ionic conduction paths can seriously degrade the impedance of the wave filter at resonance.

Referring once again to FIG. 46, there will typically be a laser weld (not shown) electrically and mechanically connecting the tip conductor 114 to pin 152. There is also a laser weld 188 connecting pin 154 to a weld sleeve 190 of the translatable seal assembly 184. The weld sleeve 190 may be attached to the pin 154 in any known technique including laser welding, bonding, crimping, adhering, brazing, other forms of welding, or any other suitable method. The weld sleeve 190 is typically laser welded to the helix electrode 122. During transvenous insertion, the active fixation helix tip electrode 122 is retracted (as shown) so that it will not inadvertently stab or poke into body tissues during lead insertion. When the physician has positioned it in the desirable location (perhaps inside the cardiac right ventricle), then the physician takes a special tool and twists the proximal end of lead body 178 tip conductor 114 which causes the entire conductor 114 and casing subassembly 182 to rotate. As the distal helix electrode 122 rotates, it engages a guide 192 which causes the helix 122 to extend and screw into body tissue. The guide 192 may be formed as part of the collar 180 and engages the tip electrode 122 when the tip conductor 114 is rotated. The rotation causes the helical tip electrode 122 to rotate within the collar 180 and thereby translate in a forward manner. At the same time the tip electrode 122 is advancing relative to the collar 180, it is engaging with body tissue by being screwed directly into the tissue forming an attachment. The tip electrode 122 can be rotated in the opposite direction by the tip conductor 114 and thereby disengaged from the tissue for removal and/or reattachment at a different location. This is a method of active affixation which is well known in the art.

The flexible seal 194 of FIG. 46 slides against the interior of the collar 180 thereby preventing the entrance of ionic body fluids into the inside of the lead body 178. The seal 194 may be bonded, molded, adhered, or formed onto the weld sleeve 190 by any suitable means. The seal 194 can be formed in a multitude of ways appreciated by those skilled in the art, such as multiple wipers, o-rings, thin disks or sheets, and various molded profiles.

There is a secondary optional O-ring seal 196 as shown in FIG. 46. The optional O-ring seal 196 is disposed between the inside diameter of the lead collar 180 and the outside diameter of the translatable housing and multilayer helical wave filter 126. The purpose of seal 194 and the O-ring seal 196 is to ensure that ionic body fluids cannot be disposed across the important electrical path between pins 152 and 154. Ionic body fluids can represent an undesirable parallel path as low as 80 ohms. Over time, due to bulk permeability, body fluids will penetrate into the interior of the lead body 178. However, this is an osmotic type of action. The resulting fluids that would occur over long periods of time inside the lead body 178 would be distilled and free of ionic contaminants (de-ionized). This means that they would be less conductive of high frequency electrical signals from one end to the other of the multilayer helical wave filter 182, 126. The presence of optional O-ring 196 is desirable in that it also presents a high impedance to such a parallel circuit path. The casing 182,126 may also have a conformal insulative coating (not shown) for further electrically isolating terminals 152 and 154 such that a parallel path through body fluid is further impeded. The insulative coating may be formed from any suitable material, such as a dielectric material, including, but not limited to parylene, ETFE, PTFE, polyamide, polyurethane and silicone. It will be understood that the exemplary embodiment of FIG. 46 may work with or without such coatings. The casing 182 may be a metallic and hermetically container or any biocompatible insulative material. The multilayer helical waver filter of the present invention is hollow on the inside for convenient insertion of additional wires.

From the foregoing it will be appreciated that, the multilayer helical wave or bandstop filters 126 of the present invention resonate at one or more frequencies and thereby provide a very high impedance at a selected resonant frequency(ies) or range of frequencies, and comprises an elongated conductor 140 having at least one planar surface. The elongated conductor includes a first helically wound segment 142 having a first end and a second end forming a first inductor component, a return wire or return coil 144, and a second helically wound segment 146 having a first end and a second end forming a second inductor component. The first and second helically wound segments share a common longitudinal axis and are wound in the same direction wherein induced currents also flow in the same direction. The return wire or return coil 144 extends substantially to the length of the first and second helically wound inductor segments to connect the second end of the first helically wound segment to the first end of the second helically wound segment.

The planar surface or surfaces of the first inductor faces the planar surface or surfaces of the second inductor and are coated with a dielectric insulative layer. Parasitic capacitance is formed between the planar surfaces of both the inner and outer inductors and adjacent coils. The combination of the inductors and the parasitic capacitances form a multi-helical wave filter, which in preferred embodiments act as a bandstop filter. By providing a very high impedance at MRI pulsed frequencies, the multilayer helical wave filter of the present invention prevents the leadwire and/or its distal electrodes that are in contact with body tissue from overheating.

Although several embodiments of the invention have been described in detail for purposes of illustration, various modifications of each may be made without departing from the spirit and scope of the invention. Accordingly, the invention is not to be limited, except as by the appended claims.

What is claimed is:

1. An implantable lead having a length extending to and meeting with a distal lead end and a proximal lead end that is configured to be electrically connectable to an active medical device, the lead comprising a first multilayer helical wave filter in series with the lead somewhere along the length thereof, the first multilayer helical wave filter formed from an electrical conductor and comprising:
    a) a first helically wound segment having at least one first planar or round surface, a first end and a second end, the first helically wound segment forming a first inductive component;
    b) a first return segment comprising a first return segment first end connected to the second end of the first helically wound segment and extending to a first return segment second end connected to a first end of the second helically wound segment;
    c) a second helically wound segment having at least one second planar or round surface and comprising the first end connected to the second end of the first return segment and extending to a second end adjacent to the second end of the first helically wound segment and the first return segment first end, the second helically wound segment forming a second inductive component, wherein a portion of the first return segment residing in an axial relationship with respect to a longitudinal extent of the winds of the first and second helically wound segments resides entirely inside or outside both of them; and
    d) a first dielectric material disposed between the first and second planar or round surfaces facing each other, thereby forming a first capacitance between adjacent coils of the first and second helically wound segments;
    e) wherein the wave filter has a Q with a 3 db bandwidth that is at least 10 kHz.

2. The implantable medical lead of claim 1, further comprising a second multilayer helical wave filter in series with a second lead conductor somewhere along a second length thereof, the second wave filter comprising:
    a) a third helically wound segment having at least one third planar or round surface, a first end and a second end, the third helically wound segment forming a third inductive component;
    b) a second return segment comprising a second return segment first end connected to the second end of the third helically wound segment and extending to a second return segment second end connected to a first end of the fourth helically wound segment;
    c) a fourth helically wound segment having at least one fourth planar or round surface and comprising the first end connected to the second end of the second return segment and extending to a second end adjacent to the second end of the third helically wound segment and the second return segment first end, the fourth helically wound segment forming a second inductive component, wherein a portion of the second return segment residing in an axial relationship with respect to the longitudinal extent of the winds of the third and fourth helically wound segments resides entirely inside or outside both of them; and d) a second dielectric material disposed between the third and fourth planar or round surfaces facing each other, thereby forming a third capacitance between adjacent coils of the third and fourth helically wound segments, the first and second dielectric materials being the same or different;

e) wherein the second wave filter has a Q with a 3 db bandwidth that is at least 10 kHz.

3. The implantable medical lead of claim 1, wherein induced RF current paths in the first and second helically wound segments will be in the same direction.

4. The implantable medical lead of claim 1, including the first dielectric material being contacted to all surfaces or sides of the first and second helically wound segments.

5. The implantable medical lead of claim 1 wherein a first inductance formed by the first and second helically wound segments is electrically in parallel with the first capacitance between the facing first and second planar or round surfaces.

6. The implantable medical lead of claim 1, including at least one of the group consisting of a tip electrode, a ring electrode, a paddle electrode, and catheter electrode and wherein the first and second helically wound segments are disposed at, adjacent to, or within at least one of the tip electrode, the ring electrode, the paddle electrode, and the catheter electrode.

7. The implantable medical lead of claim 1, wherein the 3 dB bandwidth is resonant at a selected RF diagnostic or therapeutic frequency.

8. The implantable medical lead of claim 1, wherein the first return segment is coiled entirely inside or outside of the first and second helically wound segments.

9. The implantable medical lead of claim 1, wherein one of the first and second helically wound segments is radially inside the other one of them.

10. The implantable medical lead of claim 1, wherein the first and second helically wound segments are co-radially disposed about a common longitudinal axis in a side-by-side relationship.

11. The implantable medical lead of claim 1, wherein the electrical conductor has a rectangular or a square cross-sectional configuration.

12. The implantable medical lead of claim 1, wherein the first dielectric material is selected from the group consisting of polyimide, aromatic polyimide, liquid crystal polymer, PTFE, PEEK, ETFE, Parylene, tantalum oxides, any nano-dielectric coating, PFA, FEP, Polyurethane, polyurethane with self-bonding overcoat, polyamide, polyvinyl acetal, polyvinyl acetal overcoated with polyamide, polyurethane overcoated with polyamide, epoxy, polyester (amide) (imide) overcoated with polyamide, polyester (amide) (imide), silicone-treated glass fiber, polyamide-imide, thermoplastic compounds, polyvinylchloride (PVC), polylefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, and a crosslinked polyalkene.

13. The implantable medical lead of claim 1, further including:

a) a third return segment comprising a third return segment first end connected to the second end of the second helically wound segment and extending to a third return segment second end connected to a first end of a fifth helically wound segment; and b) the fifth helically wound segment having at least one fifth planar or round surface and comprising the first end connected to the second end of the third return segment and extending to a second end adjacent to the second ends of the first and second helically wound segments and the first return segment first end, the fifth helically wound segment forming a third inductive component, wherein a planar or round surface of the fifth helically wound segment faces a planar or round surface of the second helically wound segment; and c) a third dielectric material disposed between the facing planar or round surfaces of the second and fifth helically wound segments, the first and third dielectric materials being the same or different.

14. The implantable medical lead of claim 1, wherein a first dielectric constant of the first dielectric material ranges from 2 to 50.

15. The implantable medical lead of claim 1, wherein the first multilayer helical wave filter resonates across a plurality of MRI RF pulsed frequencies or frequency ranges.

16. The implantable medical lead of claim 1, wherein the first multilayer helical wave filter resonates at a selected RF frequency and one or more of its harmonic frequencies.

17. The implantable medical lead of claim 1, wherein the first helically wound segment has a different cross-sectional area than the second helically wound segment.

18. The implantable medical lead of claim 1 wherein the first helically wound segment has a different number of turns than the second helically wound segment.

19. The implantable medical lead of claim 1, including electrical insulation for attenuating RF currents in body fluids or tissues from degrading impedance of the first multilayer helical wave filter at resonance.

20. The implantable medical lead of claim 19, wherein the insulation is contiguous with an overall insulation of the implantable lead.

21. The implantable medical lead of claim 19, further comprising an electrically insulative sleeve disposed about the first wave filter.

22. The implantable lead of claim 1 wherein the wave filter has at least the first dielectric material with a first dielectric constant disposed between a first portion of the first and second helically wound segments and a fourth dielectric material with a fourth dielectric constant disposed between the remainder of the first and second helically wound segments, and wherein the first and fourth dielectric materials are different.

23. The implantable lead of claim 13 wherein the first dielectric material with a first dielectric constant is disposed between the first and second helically wound segments and the third dielectric material with a third dielectric constant is disposed between the second and fifth helically wound segments, and wherein the first and third dielectric materials are the same or different.

24. The implantable lead of claim 1 wherein a second capacitance is provided between adjacent coils of the first and second helically wound segments.

25. The implantable medical lead of claim 24 wherein a second inductance created by the first and second helically wound segments is electrically in parallel with the second capacitance between the first and the second helically wound segments.

26. The implantable lead of claim 1 wherein the first end of the first helically wound segment is electrically connected to the distal end of the lead conductor and the second end of the second helically wound segment is electrically coupled to an electrode.

27. The implantable lead of claim 1 wherein the first end of the helically wound segment is configured to be electrically connectable to an external portion of a terminal pin of a hermetic seal and the second end of the second helically wound segment is electrically coupled to the proximal end of the lead conductor.

28. The implantable lead of claim 2 wherein induced RF current paths in the third and fourth helically wound segments flow in the same direction along the longitudinal axis.

29. The implantable lead claim 13 wherein induced RF current paths in the first, second and fifth helically wound segments flow in the same direction along the longitudinal axis.

30. The implantable medical lead of claim 1 wherein the 3 dB bandwidth is measurable in a 50-ohm balanced system using a spectrum or network analyzer.

31. The multilayer helical wave filter of claim 2 wherein a fourth capacitance is formed between adjacent coils of the third and fourth helically wound segments.

32. The implantable medical lead of claim 2 wherein the second dielectric material is selected from the group consisting of polyimide, aromatic polyimide, liquid crystal polymer, PTFE, PEEK, ETFE, Parylene, tantalum oxides, any nano-dielectric coating, PFA, FEP, Polyurethane, polyurethane with self-bonding overcoat, polyamide, polyvinyl acetal, polyvinyl acetal overcoated with polyarnide, polyurethane overcoated with polyamide, epoxy, polyester (amide) (imide) overcoated with polyamide, polyester (amide) (imide), silicone-treated glass fiber, polyamide-imide, thermoplastic compounds, polyvinylchloride (PVC), polylefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, and a crosslinked polyalkene.

33. The implantable medical lead of claim 13 wherein the third dielectric material is selected from the group consisting of polyimide, aromatic polyimide, liquid crystal polymer, PTFE, PEEK, ETFE, Parylene, tantalum oxides, any nano-dielectric coating, PFA, FEP, Polyurethane, polyurethane with self-bonding overcoat, polyamide, polyvinyl acetal, polyvinyl acetal overcoated with polyamide, polyurethane overcoated with polyarnide, epoxy, polyester (amide) (imide) overcoated with polyamide, polyester (amide) (imide), silicone-treated glass fiber, polyamide-imide, thermoplastic compounds, polyvinylchloride (PVC), polylefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, and a crosslinked polyalkene.

34. A multilayer helical wave filter that is configured to be connectable in series with an implantable lead of an active medical device, the wave filter comprising first and second helically wound segments wound in the same longitudinal direction and sharing a common longitudinal axis, the multilayer helical wave filter formed from an electrical conductor and comprising:
   a) the first helically wound segment having at least one first planar or round surface, a first end and a second end, the first helically wound segment forming a first inductive component;
   b) a first return segment comprising a first return segment first end connected to the second end of the first helically wound segment and extending to a first return segment second end connected to a first end of the second helically wound segment;
   c) the second helically wound segment having at least one second planar or round surface and comprising the first end connected to the second end of the first return segment and extending to a second end adjacent to the second end of the first helically wound segment and the first return segment first end, the second helically wound segment forming a second inductive component, wherein a portion of the first return segment residing in an axial relationship with respect to a longitudinal extent of the winds of the first and second helically wound segments resides entirely inside or outside both of them; and
   d) a first dielectric material disposed between the first and second planar or round surfaces facing each other, thereby forming a first capacitance between adjacent coils of the first and second helically wound segments;
   e) wherein the wave filter has a Q with a 3 dB bandwidth that is at least 10 kHz.

35. The multilayer helical wave filter of claim 34, including the first dielectric material being contacted to all surfaces or sides of the first and second helically wound segments.

36. The multilayer helical wave filter of claim 34, wherein a first inductance formed by the first and second helically wound segments is electrically in parallel with the first capacitance between the facing first and second planar or round surfaces.

37. The multilayer helical wave filter of claim 34 being configured to be disposed at, adjacent to, or within at least one of the group consisting of a tip electrode, a ring electrode, a paddle electrode, and a catheter electrode.

38. The multilayer helical wave filter of claim 34, wherein one of the first and second helically wound segments is disposed radially inside the other.

39. The multilayer helical wave filter of claim 34, wherein the first and second helically wound segments are co-radially disposed about the common longitudinal axis in a side-by-side relationship.

40. The multilayer helical wave filter of claim 34, wherein the electrical conductor has a rectangular or a square cross-sectional configuration.

41. The multilayer helical wave filter of claim 34, wherein the first dielectric material is selected from the group consisting of polyimide, aromatic polyimide, liquid crystal polymer, PTFE, PEEK, ETFE, Parylene, tantalum oxides, any nano-dielectric coating, PFA, FEP, Polyurethane, polyurethane with self-bondina overcoat, polyamide, polyvinyl acetal, polyvinyl acetal overcoated with polyamide, polyurethane overcoated with polyamide, epoxy, polyester (amide) (imide) overcoated with polyamide, polyester (amide) (imide), silicone-treated glass fiber, polyamide-imide, thermoplastic compounds, polyvinylchloride (PVC), polylefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, and a crosslinked polyalkene.

42. The multilayer helical wave filter of claim 34 further including:
   a) a second return segment comprising a second return segment first end connected to the second end of the second helically wound segment and extending to a second return segment second end connected to a first end of a third helically wound segment; and
   b) the third helically wound segment having at least one third planar or round surface and comprising the first end connected to the second end of the second return segment and extending to a second end adjacent to the second ends of the first and second helically wound segments and the first return segment first end, the third helically wound segment forming a third inductive component, wherein a planar or round surface of the third helically wound segment faces a planar or round surface of the second helically wound segment; and
   c) a second dielectric material disposed between facing planar or round surfaces of the second and third helically wound segments, the first and second dielectric materials being the same or different.

43. The multilayer helical wave filter of claim 34, wherein a first dielectric constant of the first dielectric material ranges from 2 to 50.

44. The multilayer helical wave filter of claim 34 being resonant at a plurality of MRI RF pulsed frequencies or frequency ranges.

45. The multilayer helical wave filter of claim 34 being resonant at a selected RF frequency and one or more of its harmonic frequencies.

46. The multilayer helical wave filter of claim 34, wherein the first helically wound segment has a different cross-sectional area than the second helically wound segment.

47. The multilayer helical wave filter of claim 34, wherein the first helically wound segment has a different number of turns than the second helically wound segment.

48. The multilayer helical wave filter of claim 34, including electrical insulation for attenuating RF currents in body fluids or tissues from degrading impedance of the multilayer helical wave filter at resonance.

49. The wave filter of claim 34 further comprising an electrically insulative sleeve disposed about the first wave filter.

50. The multilayer helical wave filter of claim 34 wherein at least the first dielectric material with a first dielectric constant is disposed between a first portion of the first and second helically wound segments and a third dielectric material with a third dielectric constant is disposed between the remainder of the first and second helically wound segments, and wherein the first and third dielectric materials are different.

51. The multilayer helical wave filter of claim 42 wherein the first dielectric material with a first dielectric constant is disposed between the first and second helically wound segments and the second dielectric material with a second dielectric constant is disposed between the second and third helically wound segments, and wherein the first and second dielectric materials are the same or different.

52. The multilayer helical wave filter of claim 34 wherein a second capacitance is provided between adjacent coils of the first and second helically wound segments.

53. The multilayer helical wave filter of claim 52 wherein a second inductance created by the first and second helically wound segments is electrically in parallel with the second capacitance between the first and the second helically wound segments.

54. The multilayer helical wave filter of claim 34 wherein the 3 dB bandwidth is measurable in a 50-ohm balanced system using a spectrum or network analyzer.

55. The multilayer helical wave filter of claim 52 wherein the 3 dB bandwidth is measurable in a 50-ohm balanced system using a spectrum or network analyzer.

56. A multilayer helical wave filter that is configured to be connectable in series with an implantable lead of an active medical device, the wave filter formed from an electrical conductor and comprising:
   a) an outer helically wound segment having at least one outer planar outer surface, a first outer end and a second outer end, the outer helically wound segment forming an outer inductive component;
   b) an inner helically wound segment having at least one inner planar inner surface, a first inner end and a second inner end, the inner helically wound segment forming an inner inductive component, the inner and outer helically wound segments being wound in the same longitudinal direction and sharing a common longitudinal axis, wherein the at least one outer planar surface of the outer helically wound segment faces the at least one inner planar surface of the inner helically wound segment; and
   c) a return connecting segment connecting the second end of the outer helically wound segment to the first end of the inner helically wound segment, wherein the return connecting segment provides that current paths in the outer and inner helically wound segments will be in the same direction; and
   d) a first dielectric material disposed between the facing inner and outer planar surfaces and between adjacent coils of the outer and inner helically wound segments, thereby forming a first capacitance,
   e) wherein from the first inner end to the second inner end, the inner helically wound segment resides completely inside the outer helically wound segment.

57. The multilayer helical wave filter of claim 56 wherein the electrical conductor is coated with the first dielectric material over all surfaces or sides.

58. The multilayer helical wave filter of claim 56 wherein inductance created by the outer and inner inductive components is electrically disposed in parallel with the capacitance between the outer and inner helically wound segments.

59. The multilayer helical wave filter of claim 58 wherein inductance formed by the outer and inner inductive components is electrically disposed in parallel with the capacitance between facing planar surfaces of the outer and inner helically wound segments.

60. The multilayer helical wave filter of claim 56 wherein the electrical conductor comprises a rectangular cross-sectional configuration, or a square cross-sectional configuration.

61. The multilayer helical wave filter of claim 56 wherein the first dielectric material is selected from the group consisting of polyimide, aromatic polyimide, liquid crystal polymer, PTFE, PEEK, ETFE, Parylene, tantalum oxides, any nano-dielectric coating, PFA, FEP, Polyurethane, polyurethane with self-bonding overcoat, polyamide, polyvinyl acetal, polyvinyl acetal overcoated with polyamide, polyurethane overcoated with polyamide, epoxy, polyester (amide) (imide) overcoated with polyamide, polyester (amide) (imide), silicone-treated glass fiber, polyamide-imide, thermoplastic compounds, polyvinylchloride (PVC), polyolefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, or a crosslinked polyalkene.

62. The multilayer helical wave filter of claim 56 wherein the return connecting segment extends within or exteriorly of the outer helically wound segment and the inner helically wound segment.

63. The multilayer helical wave filter of claim 56 wherein the return connecting segment is coiled exteriorly or interiorly of the outer and inner helically wound segments.

64. The multilayer helical wave filter of claim 56 including a third helically wound segment having a first end and a second end and forming a third inductive component, the outer, inner and third helically wound segments being wound in the same longitudinal direction, wherein a planar surface of the third helically wound segment faces a planar surface of the inner helically wound segment, wherein a second return connecting segment connects the second end of the inner helically wound segment to the first end of the third helically wound segment, and including a second dielectric material disposed between facing planar surfaces of the inner and third helically wound segments, the first and second dielectric materials being the same or different.

65. The multilayer helical wave filter of claim 56 wherein the wave filter comprises a bandstop filter.

66. The multilayer helical wave filter of claim 56 wherein induced RF current paths in the inner and outer helically wound segments will be in the same direction.

67. The multilayer helical wave filter of claim 56 wherein a second inductance created by the inner and outer helically wound segments is electrically in parallel with a second capacitance between the inner and outer helically wound segments.

68. The multilayer helical wave filter of claim 67 wherein a first inductance formed by the inner and outer helically wound segments is electrically in parallel with the first capacitance between the facing inner and outer planar surfaces.

69. The multilayer helical wave filter of claim 56 having a 3 dB bandwidth that is resonant at a selected RF diagnostic or therapeutic frequency.

70. The multilayer helical wave filter of claim 56 wherein a Q of the wave filter has a 10 dB bandwidth that is at least 100 kHz.

71. The multilayer helical wave filter of claim 56 wherein a dielectric constant of the first dielectric material ranges from 2 to 50.

72. The multilayer helical wave filter of claim 56 wherein at least the first dielectric material with a first dielectric constant is disposed between a first portion of the inner and outer helically wound segments and a third dielectric material with a third dielectric constant is disposed between the remainder of the inner and outer helically wound segments, and wherein the first and third dielectric materials are different.

73. An implantable lead having a length extending to and meeting with a distal lead end and a proximal lead end that is configured to be electrically connectable to an active medical device, the lead comprising a first multilayer helical wave filter in series with the lead somewhere along the length thereof, the first multilayer helical wave filter formed from an electrical conductor and comprising:

a) a first helically wound segment having at least one first planar or round surface, a first end and a second end, the first helically wound segment forming a first inductive component;
b) a first return segment comprising a first return segment first end connected to the second end of the first helically wound segment and extending to a first return segment second end connected to a first end of the second helically wound segment;
c) a second helically wound segment having at least one second planar or round surface and comprising the first end connected to the second end of the first return segment and extending to a second end adjacent to the second end of the first helically wound segment and the first return segment first end, the second helically wound segment forming a second inductive component, wherein a portion of the first return segment residing in an axial relationship with respect to a longitudinal extent of the winds of the first and second helically wound segments resides entirely inside or outside both of them; and
d) a first dielectric material disposed between the first and second planar or round surfaces facing each other, thereby forming a first capacitance between adjacent coils of the first and second helically wound segments;
e) wherein the Q of the wave filter has a 10 dB bandwidth that is at least 100 kHz.

74. The implantable medical lead of claim 73 wherein the 10 dB bandwidth of the wave filter is at least 0.5 MHz.

75. A multilayer helical wave filter that is configured to be connectable in series with an implantable lead of an active medical device, the wave filter comprising first and second helically wound segments wound in the same longitudinal direction and sharing a common longitudinal axis, the multilayer helical wave filter formed from an electrical conductor and comprising:

a) the first helically wound segment having at least one first planar or round surface, a first end and a second end, the first helically wound segment forming a first inductive component;
b) a first return segment comprising a first return segment first end connected to the second end of the first helically wound segment and extending to a first return segment second end connected to a first end of the second helically wound segment;
c) the second helically wound segment having at least one second planar or round surface and comprising the first end connected to the second end of the first return segment and extending to a second end adjacent to the second end of the first helically wound segment and the first return segment first end, the second helically wound segment forming a second inductive component, wherein a portion of the first return segment residing in an axial relationship with respect to a longitudinal extent of the winds of the first and second helically wound segments resides entirely inside or outside both of them between adjacent coils of the first and second helically wound segments; and
d) a first dielectric material disposed between the first and second planar or round surfaces facing each other, thereby forming a first capacitance between the first and second helically wound segments;
e) wherein the wave filter has a Q with a 10 dB bandwidth that is at least 100 kHz.

76. The multilayer helical wave filter of claim 75, wherein the 10 dB bandwidth is at least 0.5 MHz.

* * * * *

UNITED STATES PATENT AND TRADEMARK OFFICE
CERTIFICATE OF CORRECTION

PATENT NO. : 8,239,041 B2
APPLICATION NO. : 13/193501
DATED : August 7, 2012
INVENTOR(S) : Kishore Kumar Kondabatni et al.

Page 1 of 1

It is certified that error appears in the above-identified patent and that said Letters Patent is hereby corrected as shown below:

In the Claims:

Column 30, line 58 delete "self-bondina" and insert --self-bonding--

Signed and Sealed this
Twenty-first Day of May, 2013

Teresa Stanek Rea
*Acting Director of the United States Patent and Trademark Office*